US008927616B2

(12) United States Patent
Thomas et al.

(10) Patent No.: US 8,927,616 B2
(45) Date of Patent: Jan. 6, 2015

(54) MODIFIED POLYMERIC MATERIALS AND METHODS OF MODIFYING POLYMERIC MATERIALS

(75) Inventors: Brian H. Thomas, Auburndale, FL (US); Donald L. Yakimicki, Warsaw, IN (US); Oludele O. Popoola, Granger, IN (US); Michael Wallick, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/882,865

(22) PCT Filed: Nov. 2, 2011

(86) PCT No.: PCT/US2011/058958
§ 371 (c)(1),
(2), (4) Date: Sep. 20, 2013

(87) PCT Pub. No.: WO2012/061497
PCT Pub. Date: May 10, 2012

(65) Prior Publication Data
US 2014/0031496 A1 Jan. 30, 2014

Related U.S. Application Data

(63) Continuation of application No. 12/938,746, filed on Nov. 3, 2010.

(51) Int. Cl.
| A61F 2/28 | (2006.01) |
| A61F 2/44 | (2006.01) |
| A61F 2/02 | (2006.01) |
| A61F 2/30 | (2006.01) |
| A61F 2/40 | (2006.01) |
| B29C 43/02 | (2006.01) |
| A61L 27/16 | (2006.01) |
| A61L 27/50 | (2006.01) |
| C08J 3/28 | (2006.01) |

(52) U.S. Cl.
CPC ............... *A61L 27/16* (2013.01); *B29C 43/02* (2013.01); *A61L 27/50* (2013.01); *C08J 3/28* (2013.01)
USPC .......... 522/126; 522/127; 522/129; 522/130; 522/134; 522/146; 623/16.11; 623/18.11; 623/19.11; 623/20.11; 623/20.14; 623/21.11; 623/22.11; 623/22.39

(58) Field of Classification Search
CPC ............ A61F 2/28; A61F 2/30; A61F 2/32; A61F 2/40; A61F 2/42; A61F 2002/28; A61F 2002/30; A61F 2002/32; A61F 2002/38; A61F 2002/40; A61F 2002/42; A61F 2250/0067; A61F 2300/606; A61F 31/10; C08F 299/02; C08F 2/50
USPC ............... 522/126, 127, 129, 130, 134, 146; 623/16.11, 18.11, 19.11, 20.11, 20.14, 623/21.11, 22.11, 22.39
See application file for complete search history.

(56) References Cited

U.S. PATENT DOCUMENTS

| 4,608,309 | A | 8/1986 | Loh et al. |
| 4,867,573 | A | 9/1989 | Tsutsui et al. |
| 5,034,265 | A | 7/1991 | Hoffman et al. |
| 5,108,424 | A | 4/1992 | Hoffman, Jr. et al. |
| 5,213,722 | A | 5/1993 | Iwasaki et al. |
| 5,234,723 | A | 8/1993 | Babacz |
| 5,370,682 | A | 12/1994 | Schmitt |
| 5,399,832 | A | 3/1995 | Tanisaki et al. |
| 5,439,984 | A | 8/1995 | Kodama et al. |
| 5,993,917 | A | 11/1999 | Pan et al. |
| 6,060,129 | A | 5/2000 | Thomas et al. |
| 6,333,029 | B1 | 12/2001 | Vuakarnam et al. |
| 6,383,301 | B1 | 5/2002 | Bell et al. |
| 6,613,432 | B2 * | 9/2003 | Zamora et al. ............... 428/409 |
| 6,803,069 | B2 | 10/2004 | Patnaik et al. |
| 6,976,952 | B1 | 12/2005 | Maini et al. |
| 7,396,582 | B2 | 7/2008 | Claude et al. |
| 7,579,077 | B2 | 8/2009 | Dubrow et al. |
| 7,771,798 | B1 | 8/2010 | Grosse et al. |
| 2003/0149126 | A1 | 8/2003 | Martakos et al. |
| 2005/0095695 | A1 | 5/2005 | Shindler et al. |
| 2005/0177103 | A1 | 8/2005 | Hunter et al. |
| 2005/0181198 | A1 | 8/2005 | David et al. |
| 2005/0181531 | A1 | 8/2005 | Kamiya et al. |
| 2005/0186243 | A1 | 8/2005 | Hunter et al. |
| 2005/0186247 | A1 | 8/2005 | Hunter |
| 2005/0215764 | A1 | 9/2005 | Tuszynski et al. |

(Continued)

FOREIGN PATENT DOCUMENTS

| DE | 4331667 A1 | 3/1995 |
| DE | 19612270 C1 | 9/1997 |

(Continued)

OTHER PUBLICATIONS

"U.S. Appl. No. 12/640,655, Non Final Office Action mailed Apr. 14, 2011", 7 pgs.
"U.S. Appl. No. 12/938,746, Examiner Interview Summary mailed Feb. 6, 2013", 3 pgs.
"U.S. Appl. No. 12/938,746, Examiner Interview Summary mailed Aug. 22, 2012", 3 pgs.
"U.S. Appl. No. 12/938,746, Response filed Jan. 29, 2013 to Restriction Rquirement mailed Nov. 29, 2012", 11 pgs.
"U.S. Appl. No. 12/938,746, Response filed May 29, 2012 to Restriction Rquirement mailed May 4, 2012", 7 pgs.
"U.S. Appl. No. 12/938,746, Response filed Oct. 10, 2012 to Restriction Rquirement mailed Jul. 10, 2012", 13 pgs.

(Continued)

*Primary Examiner* — Nathan M Nutter
(74) *Attorney, Agent, or Firm* — Schwegman Lundberg & Woessner, P.A.

(57) ABSTRACT

Methods of forming polymeric articles using plasma treated polymer resins, and orthopedic implants comprising a polymeric article wherein the polymeric article has reactive groups bonded to polymer molecules in an interior region of the polymeric article.

20 Claims, 12 Drawing Sheets

(56) References Cited

U.S. PATENT DOCUMENTS

| | | |
|---|---|---|
| 2005/0281878 A1 | 12/2005 | Cowieson et al. |
| 2006/0240064 A9 | 10/2006 | Hunter et al. |
| 2007/0041952 A1 | 2/2007 | Guilak et al. |
| 2007/0191923 A1 | 8/2007 | Weber et al. |
| 2007/0231362 A1 | 10/2007 | Perez et al. |
| 2007/0275304 A1 | 11/2007 | Friedrich et al. |
| 2008/0056923 A1 | 3/2008 | Lee et al. |
| 2008/0056928 A1 | 3/2008 | Bunce et al. |
| 2008/0145553 A1 | 6/2008 | Boulos et al. |
| 2008/0153077 A1 | 6/2008 | Henry |
| 2008/0264259 A1 | 10/2008 | Leung |
| 2008/0318026 A1 | 12/2008 | Dai et al. |
| 2008/0319137 A1 | 12/2008 | Rufner et al. |
| 2009/0035892 A1 | 2/2009 | Haji et al. |
| 2009/0060961 A1 | 3/2009 | Naruse et al. |
| 2009/0136781 A1 | 5/2009 | Damani et al. |
| 2010/0028999 A1 | 2/2010 | Nain |
| 2010/0047532 A1 | 2/2010 | Mozetic et al. |
| 2010/0106233 A1 | 4/2010 | Grant et al. |
| 2010/0151114 A1 | 6/2010 | Parrott |
| 2010/0285252 A1 | 11/2010 | Miyazawa et al. |
| 2010/0298461 A1 | 11/2010 | Lehmann et al. |
| 2012/0109301 A1 | 5/2012 | Thomas et al. |

FOREIGN PATENT DOCUMENTS

| | | |
|---|---|---|
| EP | 2039760 A1 | 3/2009 |
| WO | WO-0196407 A2 | 12/2001 |
| WO | WO-0207961 A1 | 1/2002 |
| WO | WO-0213881 A1 | 2/2002 |
| WO | WO-03091318 A1 | 11/2003 |
| WO | WO-2004030703 A2 | 4/2004 |
| WO | WO-2009002869 A2 | 12/2008 |
| WO | WO-2010031889 A1 | 3/2010 |
| WO | WO-2010043684 A1 | 4/2010 |
| WO | WO-2012061497 A1 | 5/2012 |

OTHER PUBLICATIONS

"U.S. Appl. No. 12/933,746, Restriction Requirement mailed May 4, 2012", 5 pgs.

"U.S. Appl. No. 12/938,746, Restriction Requirement mailed Jul. 10, 2012", 8 pgs.

"U.S. Appl. No. 12/938,746, Restriction Requirement mailed Nov. 29, 2012", 7 pgs.

"International Application Serial No. PCT/US2011/058958, International Preliminary Report on Patentability mailed Oct. 26, 2012", 13 pgs.

"International Application Serial No. PCT/US2011/058958, International Search Report mailed Feb. 1, 2012", 4 pgs.

"International Application Serial No. PCT/US2011/058958, Written Opinion mailed Feb. 1, 2012", 5 pgs.

Bradley, J W, et al., "Using plasma Discharges to Chemically Functionalise 3-D Tissue Engineering Scaffolds", Proceedings of the 2008 17th International Conference on Gas Discharges and Their Applications, (2009), 497-499 pgs.

Desai, et al, "Surface Modification of Polyethylene", Article; Advance Polymer Science vol. 169, (2004), 231-293 pgs.

Ju, Young Min, et al., "Beneficial Effect of Hydrophilized Porous Polymer Scaffolds in Tissue-Engineered Cartilage Formation", Applied Biomaterials, vol. 85B, (2008), 252-260 pgs.

Kaur, Satinderpal, et al., "Plasma-Induced Graft Copolmerization of Poly(methacrylic acid) on Electrospun Poly (vinylidene fluoride) Nonofiber Membrane", Langmuir, (Dec. 2007), 13085-13092 pgs.

"U.S. Appl. No. 12/938,746, Final Office Action mailed Feb. 21, 2014", 6 pgs.

"U.S. Appl. No. 12/938,746, Non Final Office Action mailed Jul. 15, 2013", 9 pgs.

"U.S. Appl. No. 12/938,746, Response filed Dec. 16, 2013 to Non-Final Office Action mailed Jul. 15, 2013", 11 pgs.

* cited by examiner 15 mm X 15 mm Square Wave Form

MODIFIED POLYMERIC MATERIALS AND METHODS OF MODIFYING POLYMERIC MATERIALS

CROSS-REFERENCE TO RELATED APPLICATION

This application is a U.S. National Stage Filing under 35 U.S.C. §371 of International Patent Application Number PCT/US2011/058958, filed on Nov. 2, 2011 and published on May 10, 2012 as WO 2012/061497 A1, which claims the benefit of U.S. patent application Ser. No. 12/938,746 filed Nov. 3, 2010, both of which are hereby incorporated herein by reference in their entireties.

FIELD OF THE DISCLOSURE

The present disclosure relates to modified polymeric materials and methods of modifying materials. The modified polymeric materials may be processed to produce bulk modified constructs or polymeric articles that have modified polymeric material located in inner portions of the constructs or throughout the articles. In particular, the present disclosure relates to plasma modified polymer powders or flakes that may be employed to produce the bulk modified constructs, methods of making and using plasma modified polymers powders and articles made from the plasma modified polymer powders. The present disclosure also relates methods of modifying porous polymers that may be processed to produce bulk modified constructs having modified polymers located at inner portions of the constructs. The present disclosure also relates to methods of compression molding that employ ultrasonic energy.

BACKGROUND

Numerous polymer-based implantable medical devices have been developed for implantation or insertion into the body. Examples of such medical devices include endoprosthetic joints, which typically include a metal or ceramic component articulating on or bearing against a polymeric article. On such endoprosthetic device is a knee prosthesis that includes a femoral knee prosthesis which articulates against a polymeric article. Such polymeric articles are typically made from, for example, polyethylene, ultra high molecular weight polyethylene (UHMWPE), polyaryletherketones, polyurethanes, or combinations and blends of such polymers.

In an effort to enhance certain characteristics of the polymeric article, such as hydrophilicity, wettability, lubricity, and wear resistance, just to name a few, the exterior or outer surfaces of the polymeric article may be modified to include or to have bonded thereto selected functional groups. Surface modification of a polymeric article is typically applied to an already formed polymeric article, which has been formed by, for example, compression molding, ram extrusion or deposition. After the polymeric article has been formed, an exterior surface is subjected to a modification process to introduce and bond functional or reactive groups to the polymer molecules on or near the exterior surface of the polymeric article. Exterior surface modification of a polymeric article may be accomplished by, for example, plasma treatment or wet or dry chemical treatments of the polymeric article's exterior surface.

In the orthopedic field, due to the articulation and load bearing functions of the polymeric article, over time, the exterior surface is subjected to increased wear. As a result the functional groups on the modified surface are worn off. When the original modified exterior surface is worn off, the inner bulk unmodified polymer material is exposed and, in effect, becomes the exterior surface, which may also be the articulating and load-bearing surface, of the polymeric article. Thus, when the modified exterior surface is worn off, the beneficial properties or characteristics provided by the functional groups and the modified surface generally are diminished if not lost.

SUMMARY

In one aspect, the present disclosure is directed to a method of forming a polymeric article suitable for use as an orthopedic implant. The method includes providing particles of a polymer resin. The particles of the polymer resin are exposed to a plasma wherein the plasma reacts with the particles of the polymer resin to bond one or more selected reactive groups to the particles. The polymer resin is then consolidated to form a polymeric article. The particles of polymer resin and the consolidated polymer article may be further processed, by for example, undergoing crosslinking, temperature treatments or machining.

In another aspect, a method of forming a polymeric article suitable for use as a medical implant includes providing a plasma modified polymer resin and consolidating the polymer resin to form a polymeric article. The particles of polymer resin and the consolidated polymer article may be further processed, by for example, undergoing crosslinking, temperature treatments or machining.

In yet another aspect, an orthopedic implant includes an article comprising a polymer. The article has an outer surface and an interior region. The polymer includes a plurality of polymer molecules that have one or more reactive groups bonded to the molecules. The reactive groups provide one or more selected properties, including but not limited to crosslinks, lubricity, wettability, hydrophobicity, hydrophilicity, selected biological response, tissue attachment, and protein binding. The polymer molecules having the reactive groups bonded thereto are located at least at the interior region of the polymeric article. In one embodiment, the article includes reactive groups located substantially throughout the interior region and at the exterior surface of the polymeric article. In other embodiments, the reactive groups are located in selective portions of the polymeric article. In still other embodiments, the article is a multilayered construction wherein one reactive group may be located in a first portion of the article and another different reactive group may be located in a second portion of the article.

In still another aspect, the present disclosure is directed to a method of forming a polymer layer on a substrate wherein the polymer layer has one or more reactive groups throughout. The method includes forming a plasma stream. At least one polymer powder and a modifier is introduced into the plasma stream, wherein the modifier reacts with the polymer in the plasma stream to produce a modified polymer powder that includes reactive groups bonded thereto. The modified polymer is deposited onto a substrate to form a polymer layer that includes reactive groups throughout.

In a further aspect, the present disclosure is directed to a method of forming an implantable polyaryletherketone substrate having reactive groups within an interior region of the substrate. The method includes providing a porous polyaryletherketone substrate. The reactive groups are bonded to interior regions of the substrate. The substrate is compressed to collapse pores in the substrate.

In another aspect, the present disclosure is directed to a method of forming a polymer article. The method includes providing a polymer. The polymer is elevated to a selected temperature and pressure. Ultrasonic energy is applied to the polymer while the polymer is at the elevated temperature and pressure.

BRIEF DESCRIPTION OF THE FIGURES

In the course of this description, reference will be made to the accompanying drawing(s), wherein.

DETAILED DESCRIPTION

Figure 1:
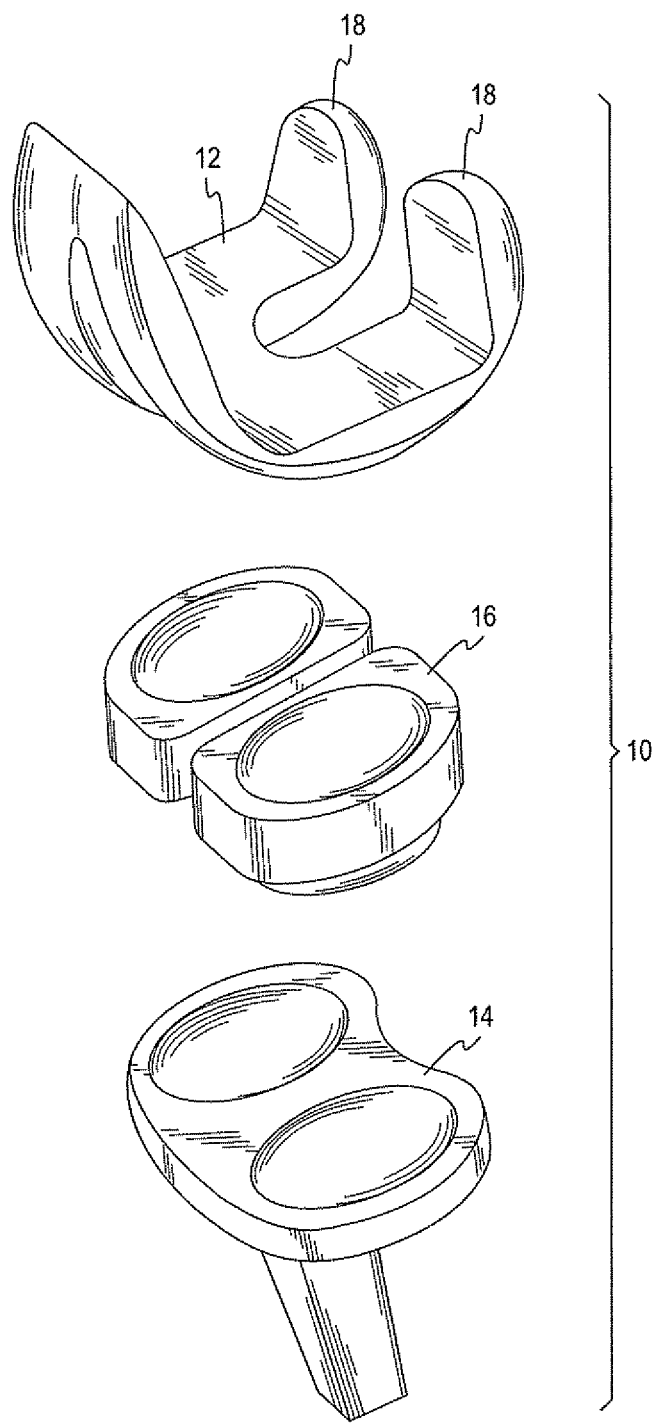
FIG. 1 is an exploded perspective view showing the components of a knee replacement system including one example of a polymeric article.

As required, detailed embodiments of the present invention are disclosed herein; however, it will be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The polymeric materials and articles disclosed herein are particularly useful in the manufacture of medical implants or medical implant systems that are permanently or temporarily implanted within a human or animal body. The polymer molecules of the polymeric articles include functional or reactive groups and that are located between or beneath the exterior surfaces or layers of the polymeric article. The functional groups of the polymer molecules may be selected to provide any number of characteristics that add to, alter or otherwise affect the physical and chemical properties of the polymeric article. For example, the functional groups may provide or assist in providing one or more of hydrophilicity, hydrophobicity, wettability, lubricity, wear resistance, crosslinking, protein binding, tissue attachment, and reduced or selected biological response. In one example, the functional groups may provide a reduced biological response to wear particles.

Further, the functional groups may be selected to bond with certain proteins within an animal or human body. As wear debris from the polymeric article is generated, the functional groups bonded to the wear particles also bond to proteins and coagulate to produce larger-sized wear debris. Larger wear particles have been shown to illicit reduced biological reactions by the human or animal body. Further, larger wear particles bonded to proteins by the reactive groups may suppress the immune response typically triggered by wear particles. Thus, reducing chronic inflammatory response and the production of UHMWPE degrading enzymes and destructive oxygen and nitrogen species.

In one embodiment, the polymer molecules having such functional groups are distributed throughout the polymeric article. As used herein, "throughout" refers to distribution of the functional groups across substantially the entire article including uniform or substantially uniform distribution and varied or irregular distribution of functional groups in the polymeric article. Alternatively, the polymer molecules having functional groups may be selectively located, distributed or dispersed in particular sections, portions or layers so that the polymeric article only includes functional groups within the selected portions, sections or layers of the polymeric article. For example, the article may include a first section or layer that includes functional groups and a second section or layer that does not have any functional groups dispersed therein. Further, different functional groups may be combined together in the same portion or layer of the polymeric article. Alternatively, different portions or layers of the polymeric article may have different functional groups to form a composite or layered structure. The composite structure may be layered so that as the exterior surface of the polymer body is worn away, different functional groups are exposed as the underlying portion or layer is exposed during the lifetime of the structure. For example, the top or exterior layer may have a first functional group and a second sub-layer or inner layer may have a second functional group. As the exterior layer is worn away, the sub-layer, having the second functional group, is exposed.

While the methods, devices and articles disclosed herein are described in relation to medical devices and medical applications, such methods and devices are not limited to such use. The methods, devices and articles may have other uses and may be used in other industries as well.

FIG. 1 illustrates one example of a prosthetic implant that may include a polymeric article of the present disclosure. In particular, FIG. 1 shows a prosthetic knee replacement system 10, which includes a femoral implant 12, a tibial implant 14 and polymeric article 16 between the femoral implant 12 and the tibial implant 14. The femoral implant 12 includes a pair of condyle members 18 that bear and articulate against the polymeric article 16. Although the polymeric article 16 in this example is shown as a component of a prosthetic knee replacement system, the polymeric articles described herein are not so limited. Polymeric articles may be a component of an implant (as shown in FIG. 1), may be used as an implant itself or may be used in other implant systems, such as, but not limited to, artificial hips and knees, cups or liners for artificial hips and knees, spinal replacement disks, artificial shoulder, elbow, feet, ankle and finger joints, mandibles, and bearings of artificial hearts, etc. The polymeric articles may also be precursors of an article such as the consolidated bulk construct, e.g. slabs, from which the article is made or shaped.

As discussed above, polymeric article 16 includes polymer molecules that have selected functional or reactive groups and are located between the exterior surfaces or in middle portions, sections or layers of polymeric article 16. The polymer molecules may be located or present throughout polymeric article 16 so that the polymeric article 16 has functional groups present substantially across the entire body of the polymeric article. Alternatively, the polymer molecules having functional groups may be located or concentrated in particular sections, portions or layers so that polymeric article 16 only includes functional groups within selected portions, sections or layers. Further, the polymeric article 16 may have different functional groups in different layers of the body to form a multilayered construct.

As the condyle members 18 repeatedly and over time articulate against the exterior surface of the polymeric article 16, the exterior surface experiences wear and eventually may be worn away. In accordance with methods and systems disclosed herein, by modifying the polymer molecules within middle portions, sections or layers of polymeric article 16, as the exterior surface of the polymeric article is worn away, the newly exposed portions or layers of the polymeric article 16 include characteristics or properties provided by these functional groups, which are now at the "new" exterior surface of the polymeric article. Thus, the polymeric article may be considered to have a renewable exterior surface. Additionally, different layers or portions of the polymeric article 16 can have different functional groups or different characteristics and/or properties such that as the polymeric article 16 undergoes wear and loses the properties provided by the functional groups, new layers or section having such characteristics and properties will be exposed over time.

The polymeric articles disclosed herein may be made from polymer powders, such as polyethylene, polyaryletherketones, polypropylene, polyurethanes, acrylics, polyethylene-co-vinyl alcohol, nylon, polysulfones, polycarbonates, and polyacrylamides or combinations thereof. One polymer powder that is commonly used in medical implants is UHMWPE. UHMWPE is a semicrystalline, linear homopolymer of ethylene, which may be produced by stereospecific polymerization with a Ziegler-Natta catalyst at low pressure (6-8 bar) and low temperature (66-80 degrees Celsius). The synthesis of nascent UHMWPE results in a fine granular powder. The molecular weight and its distribution can be controlled by process parameters such as temperature, time and pressure. UHMWPE generally has a molecular weight of at least about 2,000,000 g/mol.

Suitable UHMWPE materials for use as raw materials to form the polymeric articles of the present disclosure may be in the form of a powder, resin or flake. The polymeric articles may be prepared almost entirely from UHMWPE powder, or may be formed by combining UHMWPE powder with other suitable polymer materials. For example, the UHMWPE may be mixtures of UHMWPEs having different molecular weights. Further, the combinations may be mixtures of UHMWPE with lower molecular weight polyethylene powders, or UHMWPE with other different polymer powders such as, but not limited to, any of the other polymers listed above. In one embodiment the polymeric article may include at least about 50 w/w % UHMWPE.

Examples of suitable UHMWPE powders include GUR 1020 and GUR 1050 available from Ticona, having North American headquarters located in Florence, Ky. Suitable polymer materials for use in combination with the UHMWPE materials may include disentangled polyethylene, high pressure crystallized polyethylene, various other "super tough" polyethylene derivatives or other polymers, such as various copolymers with ethylene including poly(ethylene-co-vinyl alcohol), poly(acrylic acid-co-ethylene), and poly(ethylene-co-methacrylic acid) to name a few.

As discussed above, the functional groups, reactive groups or moieties bonded to the polymer molecules may be selected to provide or enhance any number of a variety of properties. For example, the functional groups may be selected to provide or enhance one or more of hydrophilicity, hydrophobicity, wettability, lubricity, wear resistance, crosslinking, protein binding, tissue attachment and biological response. Such functional groups may include, for example, one or more of amines, amides, imine, imide, hydroxyl, carbonyl, aldehyde, carboxylate, carboxyl, ether, ester, sulfonic, epoxide, phosphate, perfluoro, etc.

Plasma Modification

Disclosed herein are polymeric articles made of polymer groups that have been modified with selected functional groups to enhance, improve or otherwise provide the polymeric articles with selected characteristics or properties. The polymeric modified molecules may be uniformly distributed throughout the article or in selected regions or layers as desired or non-uniformly distributed, i.e., with sections or portions of the article being more/less concentrated with polymer modified by functional groups or having no functional groups at all.

The polymeric article may be provided with the properties described above in any number of ways. In one example, functional groups may be introduced into the raw material of polymer from which such articles are eventually made. One way of introducing the functional groups into the raw material is by plasma modification of polymer powder, such as polyethylene, polyaryletherketones, polypropylene, polyurethanes, acrylics, polyethylene-co-vinyl alcohol, nylon, polysulfones, polycarbonates, and polyacrylamides or combinations thereof.

In one embodiment of plasma modification, reactive gas plasmas may be used in a plasma treatment process to add functional or reactive groups to the outer surfaces of the granules flakes or particles that make up the polymer powders. The polymer powders may then be consolidated, by for example, compression molding, ram extrusion, hot isostatic pressing or any other suitable consolidation process, to create polymeric articles or bodies that may be used as or in orthopedic implants. Consolidation of the modified powders results in a polymeric article that includes functional or reactive groups in the interior regions or layers of the body. The article may also include functional groups on the exterior surface of the article. Additionally, the consolidation process may be such that the body may have layers or portions that include different functional groups.

The polymer powder may be plasma modified by any method known in the art, such as by processes that use a plasma polymer vacuum chamber or by an atmospheric plasma process that employs a blanketed carrier gas. When a vacuum chamber is utilized, the powder may be place in a rotating drum so that the powder is uniformly exposed to the plasma as the drum is rotated.

In one method of using a vacuum chamber, the chamber is evacuated to a selected pressure, and preferably a relatively low pressure. The pressure may be any suitable pressure depending on the desired application. One or more selected gases, such as, but not limited to, nitric oxide, carbon dioxide, ammonia, amine monomer (primary, secondary or tertiary) or a combination thereof, are then pumped or flowed into the chamber. The gases within the chamber are ionized by, for example, AC, DC or RF voltage, to form a plasma within the chamber. The voltage and/or power level may be such that a plasma is formed from the gases. The polymer powder is treated with the plasma for a selected period of time to form or bond one or more functional groups on the surfaces of the granules of the powder.

In an alternative embodiment, the plasma system may be an atmospheric plasma system. In this embodiment, the powder may be placed into a fluidized bed. During the atmospheric plasma treatment process the powder is passed through a reactive zone containing the reactive gas and plasma. The powder is cycled through the reactive zone a number of times to produce the desired coverage of reactive groups.

It will be appreciated that the plasma modification process is nonspecific in nature. The placement of the functional groups created on the surface(s) or some selected distance below the surface of the powder granules is non-specific. The plasma modification of the polymer powders can at least partially be controlled by varying several factors including, but not limited to: (1) the type and shape of the plasma polymer chamber/reactor; (2) the frequency of the discharge excitation voltage; (3) the power of the discharge; (4) the flow rate of gases; (5) the gas pressure within the chamber; (6) the powder temperature; (7) the particle size and geometry; and (8) the duration of the treatment. These factors may be varied to produce the desired modification for a particular application.

As discussed above, the plasma modified polymer powder may be processed to form an implantable polymeric article. Optionally, the modified polymer powder may first be blended with additives, such as antioxidants or biological agents. In another alternative embodiment, the polymer powder may be blended with an additive then plasma treated. Further, in other alternative embodiments, the functional groups may be selected so as to bond with the antioxidants or biological agents. The antioxidant may be, for example, vitamin E, and the biological agent may be, for example, an antibiotic, antimicrobial or anti-inflammatory.

The blended or unblended modified polymer powder may then be consolidated and/or compressed into a suitable form for use as (or as part of) a prosthetic device or other implant. Suitable compression and/or consolidation techniques include, for example, compression molding, direct compression molding, hot isostatic pressing, ram extrusion, high pressure crystallization, injection molding, sintering or other conventional methods of compressing and/or consolidating polymer powders. If desired, the polymeric article formed from the compressed/consolidated polymeric article may be further processed or manufactured by crosslinking, annealing, melting, heating, cooling, doping with antioxidant, doping with biological agents, milling, machining, drilling, cutting, assembling with other components, and/or other manufacturing or pre-manufacturing steps conventionally employed to manufacture implants from polymer. For example, the plasma modified powder may be subject to any of the processes of forming an article disclosed in U.S. Patent Application Publication No. US2010/0029858, published Feb. 4, 2010, and US2009/0118390, published May 7, 2009, which are incorporated herein by reference.

A multilayered construct or article may be made during the compression molding process. For instance, polymer powders having different or no modifications may be selectively placed is particular locations within the mold. For instance a first polymer resin having a first type or types of functional groups may be arranged relative to a second polymer having a second type or types of functional groups. The arranging of the first and second resins may including mixing the resins or may included selectively placing portions of the first and second resins in a desired arrangement relative to one another. For example, to make a layered construct, a first polymer powder having a first type or types of functional groups may be placed at the bottom of the mold to form a first layer. A second polymer powder having different functional groups or no functional groups (raw unmodified polymer powder) may be placed on top of the first layer to create a second layer. In other embodiments, several layers of polymer powders may be placed in the mold. Further, placement of the polymer powders is not limited to layers. The polymer powders, having different functional groups (or no functional groups) may be selectively placed in different regions or portions of the mold. Once the polymer powders have been placed in the mold, the powder is compression molded to form an article for use in or as a medical implant or a bulk material that can be shaped into such an article.

Prior to and/or after processing the implant as discussed above, the polymer may be crosslinked by any suitable crosslinking process. For example, the polymer may be crosslinked by exposure to radiation at a high radiation dose and/or a dose rate sufficient to form a crosslinked polymer. The radiation may be, for example, gamma or electron beam irradiation. In one embodiment, the polymeric article may be exposed to electron beam irradiation at a dose rate of between about 25 kGy/min and about 240 kGy/min for a total dose of between about 90 kGy and about 200 kGy. In certain embodiments, the desired radiation dose may be achieved in a single exposure step at a high dose rate. In other embodiments, a series of high dose rate irradiation steps may be employed to expose the polymer to a desired dose of radiation. The crosslinking may be conducted at any time from powder to implant and may be used in conjunction with other manufacturing processes applied to the polymeric article. Further, prior to irradiation, the polymer may be preheated.

In certain embodiments, the radiation source is electron beam radiation. Electron beam radiation exposure may be performed using conventionally available electron beam accelerators. One commercial source for such an accelerator is IBA Technologies Group, Belgium. Suitable accelerators may produce an electron beam energy between about 2 and about 50 MeV, more particularly about 10 MeV, and are generally capable of accomplishing one or more of the radiation doses and/or dosage rates reported herein. Electron beam exposure may be carried out in a generally inert atmosphere, including for example, an argon, nitrogen, vacuum, or oxygen scavenger atmosphere. Exposure may also be carried out in air under ambient conditions according to one embodiment. Gamma and x-ray radiation may also be suitable for use in alternate embodiments. The processes described herein are not necessarily limited to a specific type of source of radiation.

In another embodiment, the functional or reactive group formed on the surface the polymer powder by plasma modification may provide thermal crosslinking that can be activated with the application of heat. Such functional groups may include amines, phosphates, and sulfonates. The polymer powder may be modified to include one or more functional groups. The functional group may also serve a dual purpose, such as but not limited to, increasing lubricity. In one embodiment, the crosslinking provided by the functional group may be activated by the heat applied to the polymer powder during consolidation. When the functional group serves as a crosslinking agent, the polymeric article may or may not also be subject to other crosslinking processes, such as irradiation.

In one example, the UHMWPE powder may be modified so that the surfaces of at least some of the granules include a sulfonic acid crosslinking group bonded to the surface of the granules. Upon application of heat, such as during consolidation, the crosslinking groups undergo a dehydration reaction losing water and forming the crosslinking bond, as shown below.

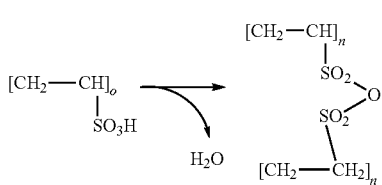

Accordingly, the crosslinked polymer may be illustrated as:

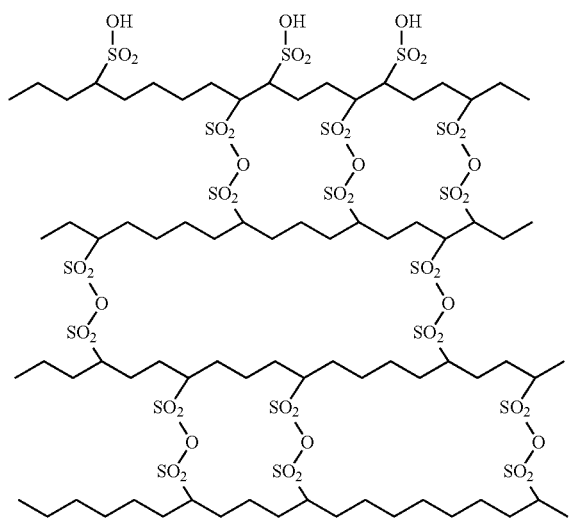 [SMILES: CCCCCCC1CCCC2CCCCCCCC(C)S(=O)(=O)OS(=O)(=O)C(C)CCC3CCCCC(CCCC(CCC(CCC)S(=O)(=O)OS(=O)(=O)C(CC)CCCCC4CCCC5CCC(C(CC)S(=O)(=O)OS(=O)(=O)C(CC)CCC(S(=O)(=O)O)C(CCC(S(=O)(=O)O)C(CCCCC(CCC)S(=O)(=O)O)S(=O)(=O)OS4(=O)=O)S(=O)(=O)OS5(=O)=O)S(=O)(=O)OS3(=O)=O)S(=O)(=O)OS1(=O)=O)S(=O)(=O)OS2(=O)=O]

During use, the surface of the polymeric article or implant is worn exposing the underlying sulfonic anhydride groups. The anhydride groups undergo a reaction with water in the body to regenerate the sulfonic acid groups, and thereby imparting and continually regenerating hydrophilicity in the surface of the polymeric article, which increases lubricity. Thus, in this example, the sulfonic groups provide or enhance crosslinking and lubricity.

The polymeric article formed from consolidation of the modified powder may also be subject to annealing. When annealing is employed, the polymeric article may be annealed at a temperature of between about 120° C. and about 230° C. for a time period of between about 1 hour and about 60 hours. The annealing may be used in conjunction with other manufacturing processes applied to the polymeric article. Alternatively or additionally, the crosslinked polymer may be subjected to the mechanical annealing processes reported in U.S. Pat. No. 6,853,772 to Muratoglu, which is incorporated herein by reference. In one embodiment, however, no pre- or post-irradiation temperature and/or annealing treatments are performed. In another embodiment, the polymeric article may be subject to an irradiation process and then annealed.

As part of the implant manufacturing process, additional components may be combined with the polymer at any time during the process reported herein. In one embodiment, tribological components such as metal and/or ceramic articulating components and/or preassembled bipolar components may be joined with the polymer. In other embodiments, metal backing (e.g. plates or shields) may be added. In further embodiments, surface components such a Trabecular Metal™ material, fiber metal, beats, Sulmesh® coating, meshes, cancellous titanium, and/or metal or polymer coatings may be added to or joined with the polymer. Sulmesh and Trabecular Metal are trademarks of Zimmer, Inc. of Warsaw, Ind. Still further, radiomarkers or radiopacifiers such as tantalum, steel and/or titanium balls, wires, bolts or pegs may be added. Further yet, locking features such as rings, bolts, pegs, snaps and/or cements/adhesives may be added. These additional components may be used to form sandwich implant designs, radiomarked implants, metal-backed implants to prevent direct bone contact, functional growth surfaces, and/or implants with locking features.

After manufacturing of the implant has been completed, it may be packaged and sterilized prior to distribution. Packaging is generally carried out using either gas permeable packaging or barrier packaging utilizing a reduced oxygen atmosphere.

A variety of implants, and in particular endoprosthetic joint replacements, may be prepared by employing the methods reported herein. Examples of such implants include artificial hips and knees, cups or liners for artificial hips and knees, spinal replacement disks, artificial shoulder, elbow, feet, ankle and finger joints, mandibles, and bearings of artificial hearts.

EXAMPLES

The following non-limiting examples illustrate various features and characteristics of the present invention, which is not to be construed or limited thereto.

Example 1

In several of the various Samples below, UHMWPE powder resins were used, which powders have been plasma modified with various gases.

Table 1 sets forth the processing parameters for Samples A-Z. Samples A, O, P and Y were control samples used for comparative analysis. As set forth in Table 1, GUR 1050 brand powder available from Ticona, having North American headquarters located in Florence, Ky. was used in samples A-X and polyether ether ketone available from Gharda, located in Newton, Pa., was used in samples Y and Z.

For Samples B-N and Q-X GUR 1050 powder was plasma treated by the gases and for the times listed in Table 1. For Samples J-N, the Sample included a blend of two powders wherein each of the two powders was treated with a different gas and then blended together at a ratio of 50%/50% by weight For example, in Sample J, one batch of GUR 1050 was treated with $N_2O$ and another batch of GUR 1050 was treated $NH_3$. The powders of the two batches were then blended together. The plasma treatment process was carried out by PVA TePla America, Corona, Calif. In all of these samples, the plasma treated powder was then consolidated by compression molding to produce a puck or generally cylindrical polymeric article having a diameter of 2.5 inches and a height of 1.5 inches. The GUR 1050 powder of control samples of A, O, P, and Y were not subjected to plasma treatment. The untreated GUR 1050 powder of these control samples were also consolidated by compression molding to produce a puck or generally cylindrical polymeric article having a diameter of 2.5 inches and a height of 1.5 inches.

Samples A-E, J-N, Y and Z received no further processing, after consolidation. The additional processing of the other Samples are as set forth below.

For Samples F-I, the compression molded pucks were then annealed in a 49A-650D oven available from Precision Quincy, located in Woodstock, Ill., at the time and temperature specified in Table 1.

For Samples O, Q-T, the compression molded pucks were irradiated at 10 MeV, at the dose rate listed in the Table 1 to a total dose of 100 kGy at Iotron Industries Canada Inc. located in Port Coquitlam, B.C., Canada.

For Samples P, U-X, the compression molded pucks were irradiated at 10 MeV, at the dose rate listed in Table 1 to a total dose of 100 kGy at Iotron Industries Canada Inc. located in Port Coquitlam, B.C., Canada. These samples were then annealed in a 49A-650D oven available from Precision Quincy at the time and temperature specified in Table 1.

TABLE 1

| SAMPLE | RAW MATERIAL | PLASMA TREATMENT | PREHEATING BEFORE IRRADIATION °C. | IRRADIATION DOSE KGY | IRRADIATION DOSE RATE | ANNEALING |
|---|---|---|---|---|---|---|
| A | GUR 1050 | N/A | N/A | N/A | N/A | N/A |
| B | GUR 1050 | $N_2O$, 50 minutes | N/A | N/A | N/A | N/A |
| C | GUR 1050 | $CO_2$, 50 minutes | N/A | N/A | N/A | N/A |
| D | GUR 1050 | $NH_3$, 50 minutes | N/A | N/A | N/A | N/A |
| E | GUR 1050 | Allylamine, 50 minutes | N/A | N/A | N/A | N/A |
| F | GUR 1050 | $N_2O$, 50 minutes | N/A | N/A | N/A | 120 C., 40 hours |
| G | GUR 1050 | $CO_2$, 50 minutes | N/A | N/A | N/A | 120 C., 40 hours |
| H | GUR 1050 | $NH_3$, 50 minutes | N/A | N/A | N/A | 120 C., 40 hours |
| I | GUR 1050 | Allylamine, 50 minutes | N/A | N/A | N/A | 120 C., 40 hours |
| J | GUR 1050 | Blend of powder treated with $N_2O$, 50 minutes and powder treated with $NH_3$, 50 minutes | N/A | N/A | N/A | N/A |
| K | GUR 1050 | Blend of powder treated with $N_2O$, 50 minutes and powder treated with $CO_2$, 50 minutes | N/A | N/A | N/A | N/A |
| L | GUR 1050 | Blend of powder treated with $N_2O$, 50 minutes and powder treated with Allylamine, 50 minutes | N/A | N/A | N/A | N/A |
| M | GUR 1050 | Blend of powder treated with $CO_2$, 50 minutes and powder treated with $NH_3$, 50 minutes | N/A | N/A | N/A | N/A |
| N | GUR 1050 | Blend of powder treated with Allylamine, 50 minutes and powder treated with $CO_2$, 50 minutes | N/A | N/A | N/A | N/A |
| O | GUR 1050 | N/A | 40 C. | 100 kGy | 30 kGy-m/min | N/A |
| P | GUR 1050 | N/A | 40 C. | 100 kGy | 30 kGy-m/min | 120 C., 40 hours |
| Q | GUR 1050 | $N_2O$, 50 minutes | 40 C. | 100 kGy | 30 kGy-m/min | N/A |
| R | GUR 1050 | $CO_2$, 50 minutes | 40 C. | 100 kGy | 30 kGy-m/min | N/A |
| S | GUR 1050 | $NH_3$, 50 minutes | 40 C. | 100 kGy | 30 kGy-m/min | N/A |
| T | GUR 1050 | Allylamine, 50 minutes | 40 C. | 100 kGy | 30 kGy-m/min | N/A |
| U | GUR 1050 | $N_2O$, 50 minutes | 40 C. | 100 kGy | 30 kGy-m/min | 120 C., 40 hours |
| V | GUR 1050 | $CO_2$, 50 minutes | 40 C. | 100 kGy | 30 kGy-m/min | 120 C., 40 hours |
| W | GUR 1050 | $NH_3$, 50 minutes | 40 C. | 100 kGy | 30 kGy-m/min | 120 C., 40 hours |
| X | GUR 1050 | Allylamine, 50 minutes | 40 C. | 100 kGy | 30 kGy-m/min | 120 C., 40 hours |
| Y | PEEK | N/A | N/A | N/A | N/A | N/A |
| Z | PEEK | $N_2O$, 50 minutes | N/A | N/A | N/A | N/A |

Results

Figure 2:
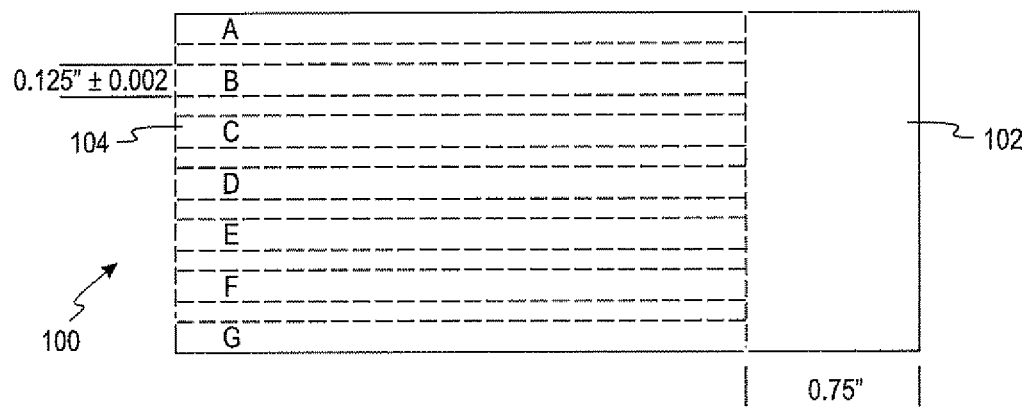
FIGS. 2 and 3 are schematic drawings of pucks made from consolidated polymer resin.
Figure 3:
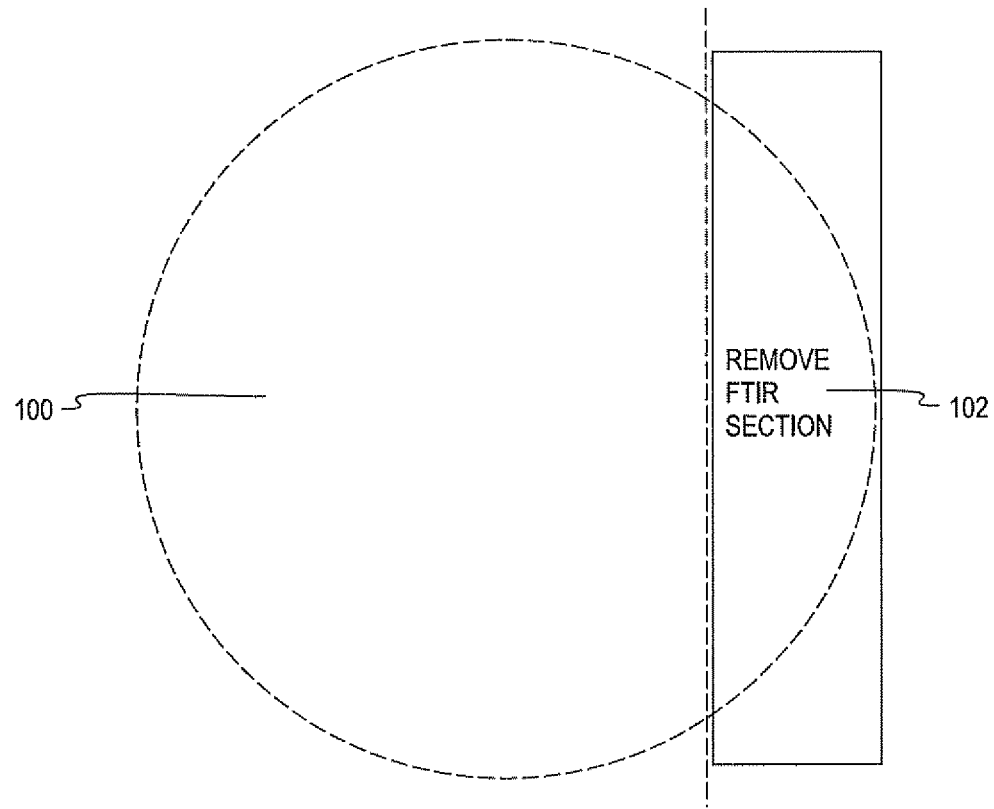

Tests were preformed on the above samples to determine the physical properties of the consolidated and processed polymer materials of the above samples. In particular, tests were conducted on sections of material taken from middle sections of the above-described compression molded puck. FIGS. 2 and 3 illustrate one example of a puck 100. A 0.75 inch portion 102 of the puck as measured from an edge of the puck was removed. Referring to FIG. 2, the puck 100 was then machined to create a plurality of flats 104 from the middle section of the puck. The flats 104 had a thickness of about 0.125±0.002 inches.

Tensile Test Results

The tensile properties of the samples were tested according to ASTMD638-02a. Tensile bars test specimens were punched from flats 104.

Tensile properties of each Sample were determined from the average of 5 runs for samples E-I and 10 runs for all other samples. An Instron Model 3345 Test System available from Instron, Norwood, Mass., USA was used to test the tensile properties of each sample. The results are listed in Table 2 with the standard deviations in parenthesis.

TABLE 2

| SAMPLE | MATERIAL | ULTIMATE TENSILE STRENGTH (MPA) | % STRAIN AT AUTOMATIC BREAK (%) | ZERO SLOPE YIELD STRESS (MPA) |
|---|---|---|---|---|
| A | GUR 1050 | 66.11 (4.25) | 404.45 (19.10) | 22.361 (0.27) |
| B | GUR 1050 N2O | 44.54 (1.83) | 332.52 (09.86) | 21.264 (0.26) |
| C | GUR1050 CO2 | 39.32 (1.66) | 301.74 (06.36) | 21.585 (0.21) |
| D | GUR 1050 NH3 | 42.27 (1.94) | 290.94 (09.65) | 22.079 (0.37) |
| E | GUR1050 Allylamine | 40.73 (2.41) | 287.50 (12.91) | 21.840 (0.46) |
| F | GUR 1050 N2O Annealed | 26.34 (2.45) | 245.01 (29.78) | 20.216 (0.31) |
| G | GUR1050 CO2 Annealed | 30.28 (2.08) | 322.72 (17.27) | 20.488 (0.95) |
| H | GUR 1050 NH3 Annealed | 30.57 (3.90) | 324.37 (80.00) | 20.720 (0.81) |
| I | GUR1050 Allylamine Annealed | 27.00 (5.42) | 247.51 (56.13) | 20.540 (0.99) |
| J | GUR 1050 N2O/NH3 | 41.68 (1.86) | 310.75 (08.99) | 21.235 (0.34) |
| K | GUR 1050 N2O/CO2 | 40.63 (0.45) | 320.14 (07.87) | 21.169 (0.25) |
| L | GUR 1050 N2O/Allylamine | 41.08 (2.66) | 309.05 (17.70) | 21.083 (0.23) |
| M | GUR 1050 CO2/NH3 | 39.27 (1.58) | 291.70 (10.48) | 21.184 (0.33) |
| N | GUR 1050 Allylamine/CO2 | 40.40 (2.76) | 291.65 (16.29) | 21.411 (0.37) |
| O | GUR 1050 100kGy | 59.35 (4.19) | 300.64 (14.13) | 23.314 (0.50) |
| P | GUR 1050 100kGy Annealed | 44.71 (3.57) | 239.29 (09.80) | 21.053 (0.20) |
| Q | GUR 1050 N2O 100kGy | 45.30 (2.09) | 252.95 (08.69) | 22.625 (0.44) |
| R | GUR 1050 CO2 100kGy | 42.41 (1.19) | 239.04 (06.26) | 23.098 (0.22) |
| S | GUR 1050 NH3 100kGy | 38.19 (0.90) | 208.10 (03.09) | 22.558 (0.18) |
| T | GUR 1050 Allylamine 100kGy | 35.26 (1.86) | 213.73 (07.29) | 22.319 (0.23) |
| U | GUR 1050 N2O 100kGy Annealed | 25.94 (5.91) | 197.45 (77.45) | 21.062 (0.73) |
| V | GUR 1050 CO2 100kGy Annealed | 26.87 (1.29) | 248.51 (11.99) | 19.851 (0.23) |
| W | GUR 1050 NH3 100kGy Annealed | 26.70 (3.36) | 217.22 (37.14) | 19.710 (0.47) |
| X | GUR 1050 Allylamine 100kGy Annealed | 25.66 (2.77) | 225.43 (14.47) | 19.580 (0.70) |
| Y | PEEK | 115.85 (06.14) | 3.61 (1.05) | 121.54 (1.91) |
| Z | PEEK Modified | 94.86 (10.29) | 2.62 (0.38) | 94.042 (12.44) |

Figure 4:
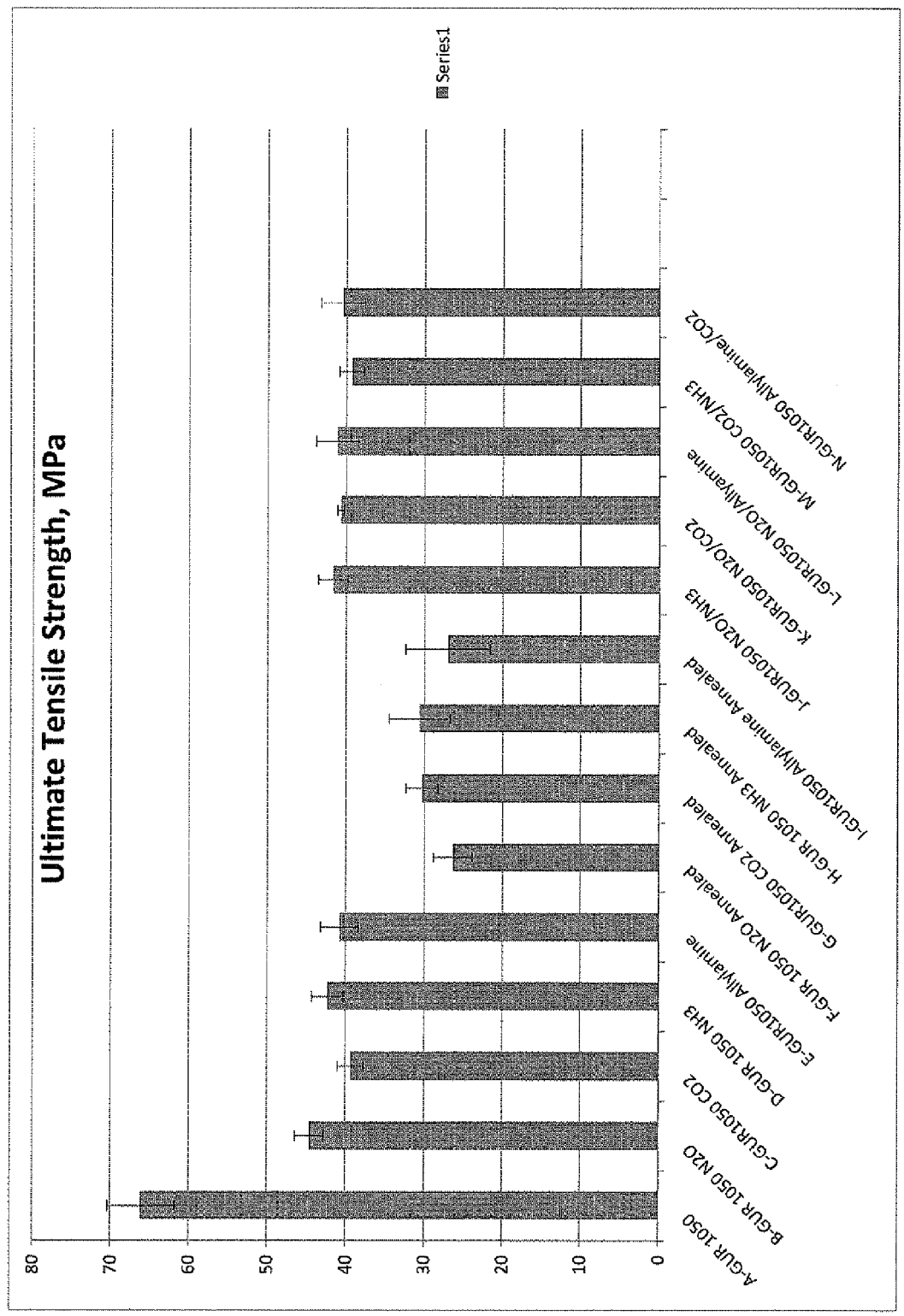
FIGS. 4 and 5 are graphs showing the ultimate tensile strength of samples made from unmodified UHMWPE powder and samples made from plasma modified UHMWPE powder.
Figure 5:
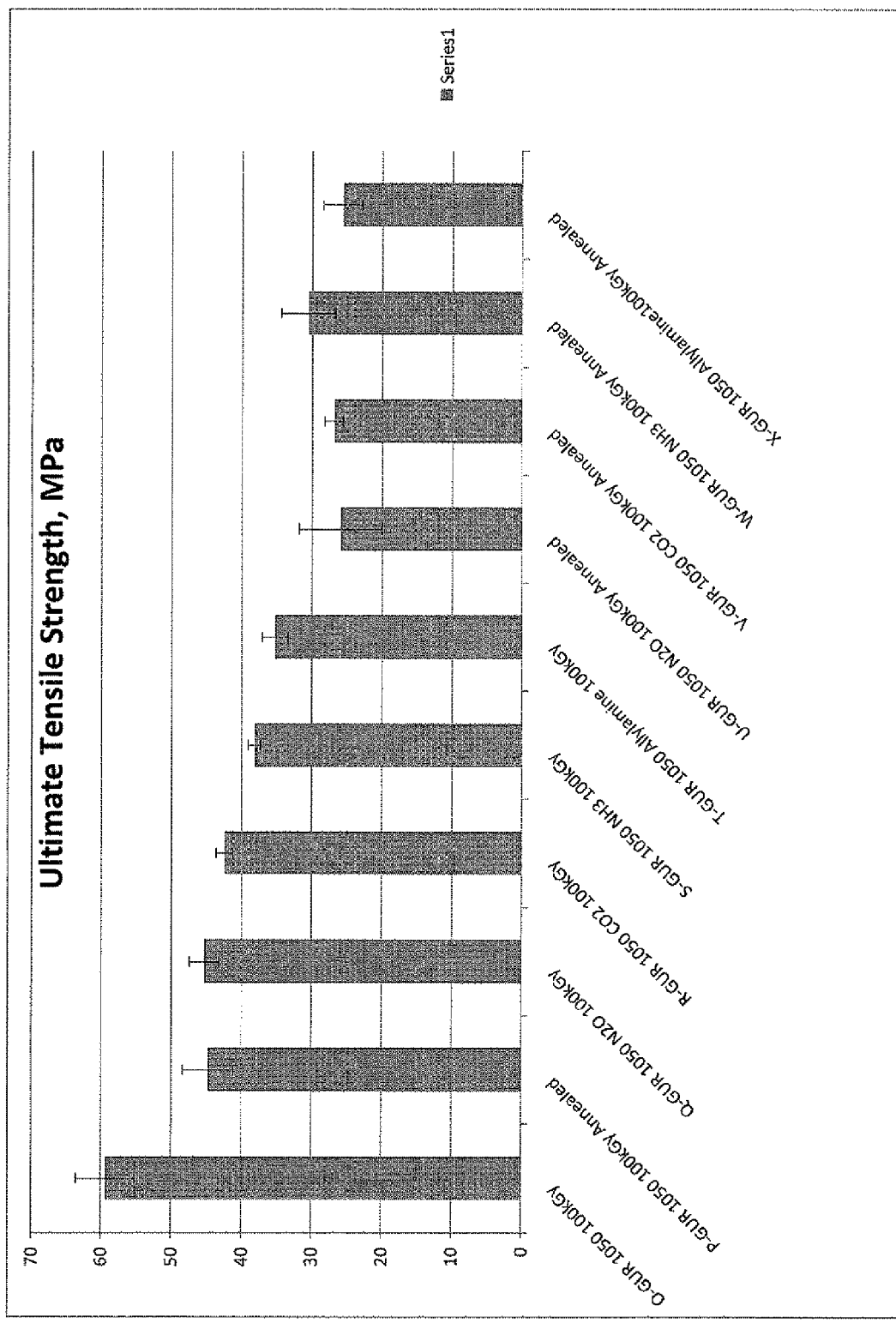
Figure 6:
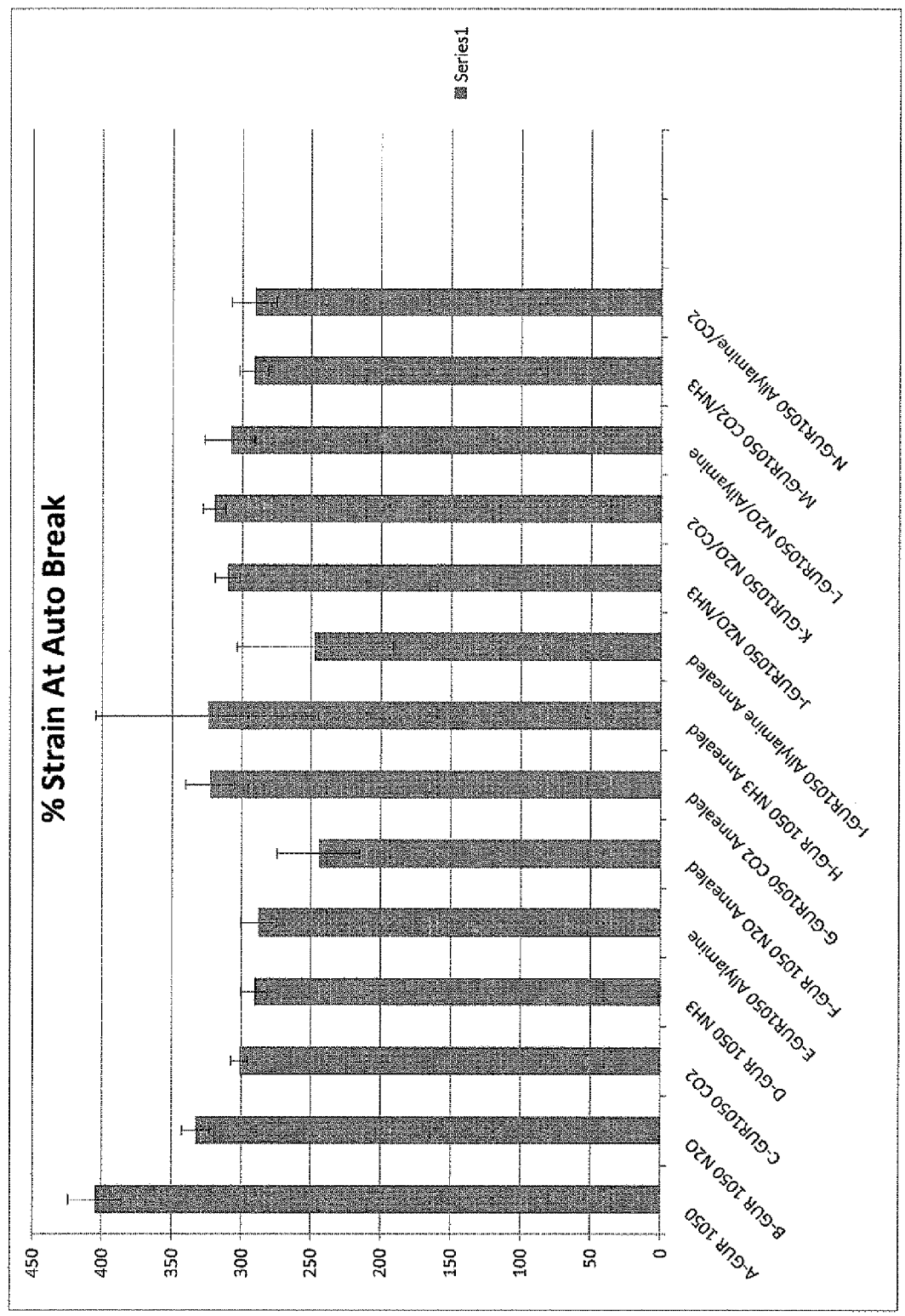
FIGS. 6 and 7 are graphs showing the percent strain at auto break of samples made from unmodified UHMWPE powder and samples made from plasma modified UHMWPE powder.
Figure 7:
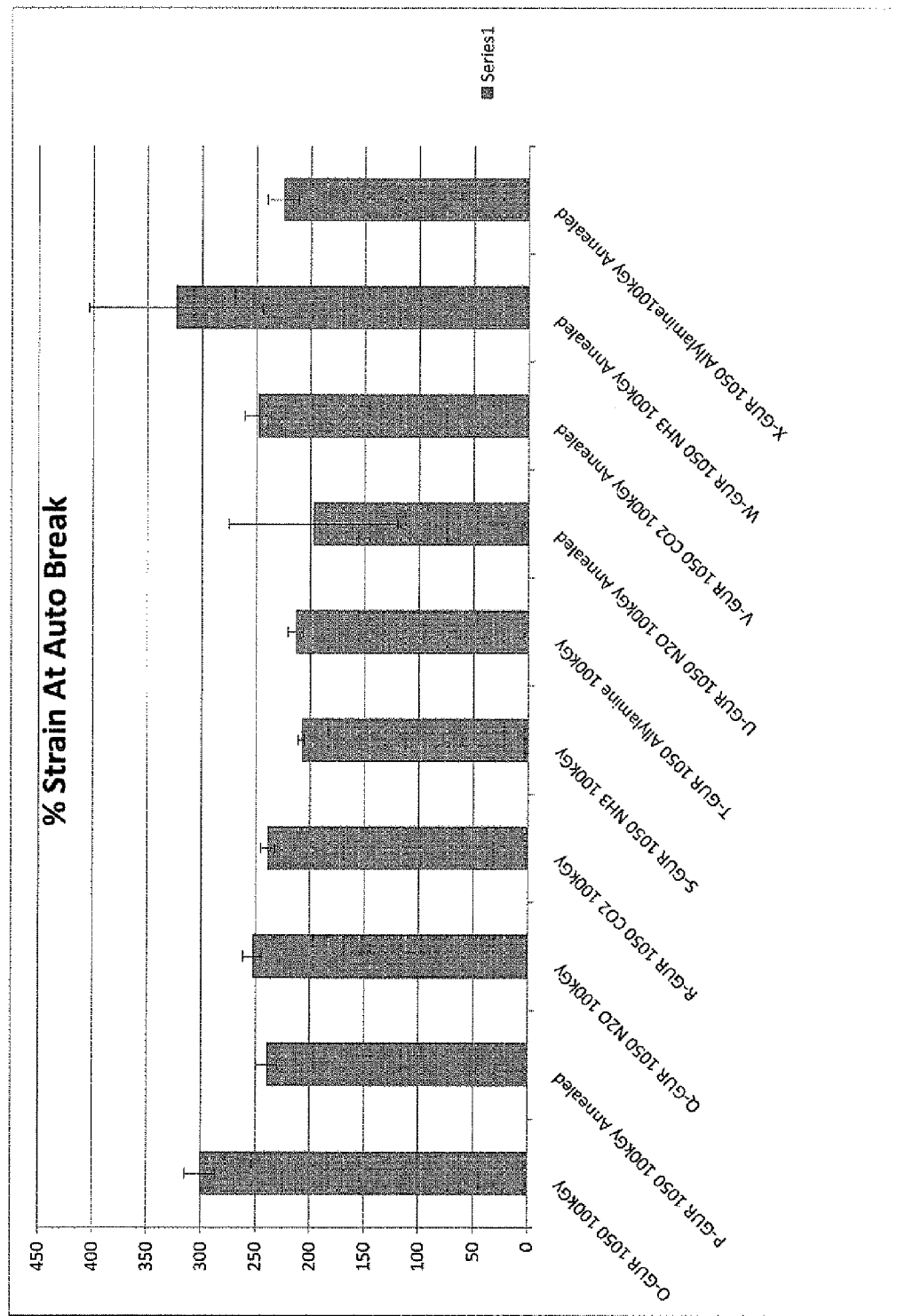

FIGS. 4-7 are bar graphs illustrating the various tensile strength properties of the samples. FIGS. 4 and 5 illustrate the Ultimate Tensile Strength of samples A-X. FIGS. 6 and 7 illustrate the Percent Strain At Automatic Break of Samples A-X.

IZOD Impact Test Results

IZOD impact testing conforming to ASTM F648-00 using double notch IZOD specimens were performed on Samples A-E and O-T. The above-described flats 104 were doubled notched and used in the IZOD impact tests.

Properties of each Sample were determined from the average of 5 runs. An IZOD Impact Tester from Tinius-Olsen was used to test the tensile properties of each sample. The results are listed in Table 3 with the standard deviation in parentheses.

TABLE 3

Figure 10:
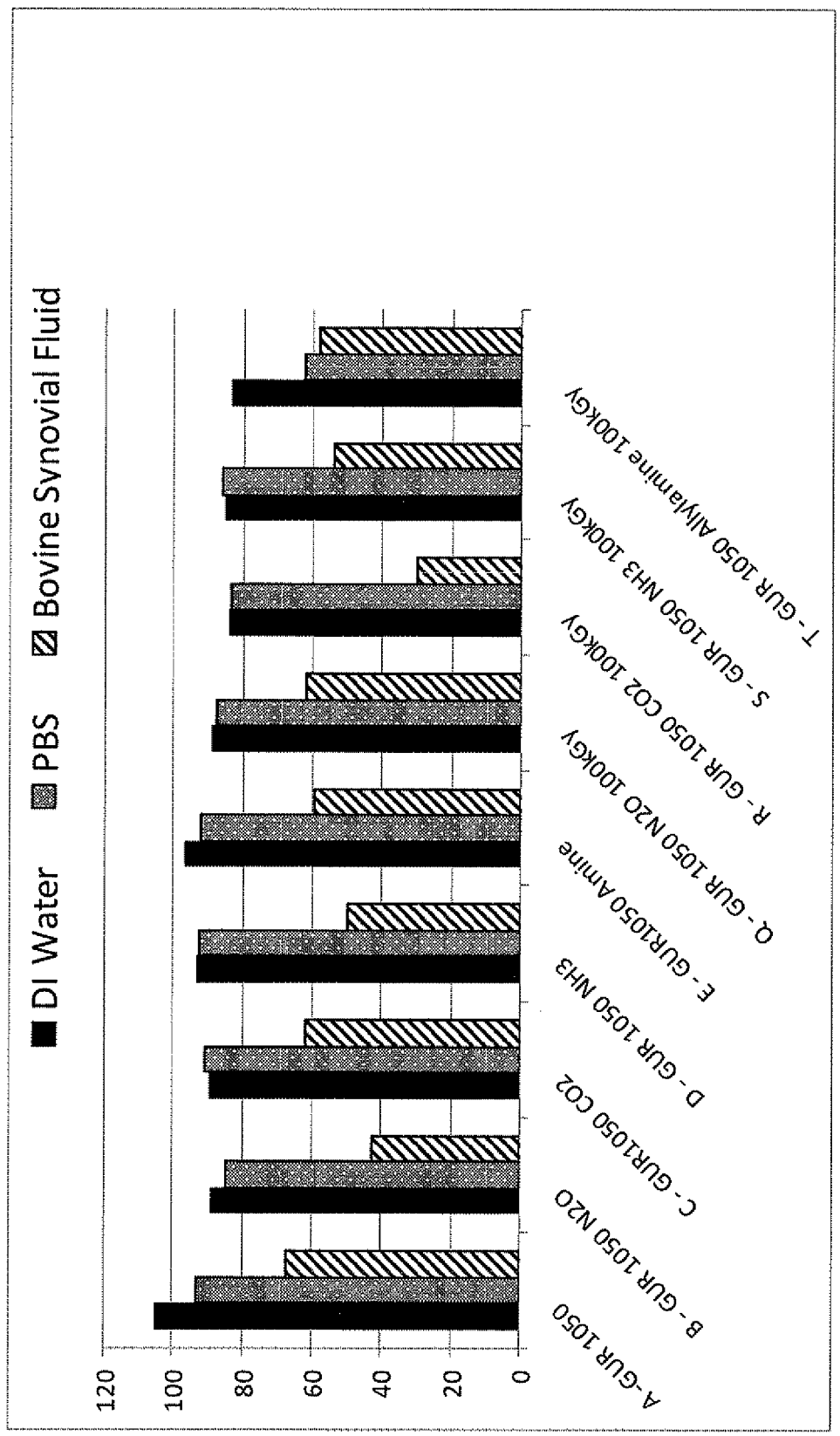
FIG. 10 is a graph showing contact angles of samples made from unmodified UHMWPE powder and samples made from plasma modified UHMWPE powder.

| SAMPLE | MATERIAL | ENERGY PER AREA (kJ/m^2) |
|---|---|---|
| A | GUR 1050 | 111.982 (3.232) |
| B | GUR 1050 N2O | 115.017 (1.717) |
| C | GUR1050 CO2 | 112.979 (3.181) |
| D | GUR 1050 NH3 | 116.109 (2.765) |
| E | GUR1050 Allylamine | 108.574 (6.555) |
| O | GUR 1050 100kGy | 75.718 (1.189) |
| P | GUR 1050 100kGy Annealed | 59.432 (2.299) |
| Q | GUR 1050 N2O 100kGy | 67.888 (1.759) |
| R | GUR 1050 CO2 100kGy | 70.948 (2.208) |
| S | GUR 1050 NH3 100kGy | 70.734 (2.244) |
| T | GUR 1050 Allylamine 100kGy | 68.583 (3.622) | ally, the contact angles were measured using a Kruss DSA 100 available from Kruss located in Matthews, N.C. The contact angle test results are shown in Table 4 and illustrated in FIG. 10.

TABLE 4

| SAMPLE | MATERIAL | Deionized $H_2O$ | PBS | Bovine Synovial Fluid |
|---|---|---|---|---|
| A | GUR 1050 | 105.3 | 92.8 | 67.5 |
| B | GUR 1050 N2O | 88.8 | 84.4 | 42.9 |
| C | GUR1050 CO2 | 89.5 | 90.4 | 62.0 |
| D | GUR 1050 NH3 | 92.8 | 92.2 | 50.1 |
| E | GUR1050 Allylamine | 96.6 | 91.6 | 59.4 |
| Q | GUR 1050 N2O 100kGy | 88.6 | 87.4 | 61.9 |
| R | GUR 1050 CO2 100kGy | 84.0 | 83.5 | 30.1 |
| S | GUR 1050 NH3 100kGy | 84.9 | 86.1 | 54.3 |
| T | GUR 1050 Allylamine 100kGy | 83.5 | 62.5 | 58.5 |

Example 2

The Samples AA-JJ shown in Table 5 below were prepared in the same manner as described above in Example 1, except that the plasma modified and unmodified GUR 1050 powder was compression molded into pucks having a diameter of 63.5 mm and a height of 52 mm. Table 5 shows the processing parameters for Samples AA-JJ.

TABLE 5

| SAMPLE | RAW MATERIAL GUR | PLASMA TREATMENT | PREHEATING BEFORE IRRADIATION °C. | IRRADIATION DOSE KGY | IRRADIATION DOSE RATE | ANNEALING |
|---|---|---|---|---|---|---|
| AA | GUR 1050 | N/A | N/A | N/A | N/A | N/A |
| BB | GUR 1050 | N$_2$O, 50 minutes | N/A | N/A | N/A | N/A |
| CC | GUR 1050 | CO$_2$, 50 minutes | N/A | N/A | N/A | N/A |
| DD | GUR 1050 | NH$_3$, 50 minutes | N/A | N/A | N/A | N/A |
| EE | GUR 1050 | Allylamine, 50 minutes | N/A | N/A | N/A | N/A |
| FF | GUR 1050 | N/A | 40 C. | 100 kGy | 30 kGy-m/min | N/A |
| GG | GUR 1050 | N$_2$O, 50 minutes | 40 C. | 100 kGy | 30 kGy-m/min | N/A |
| HH | GUR 1050 | CO$_2$, 50 minutes | 40 C. | 100 kGy | 30 kGy-m/min | N/A |
| II | GUR 1050 | NH$_3$, 50 minutes | 40 C. | 100 kGy | 30 kGy-m/min | N/A |
| JJ | GUR 1050 | Allylamine, 50 minutes | 40 C. | 100 kGy | 30 kGy-m/min | N/A |

Figure 8:
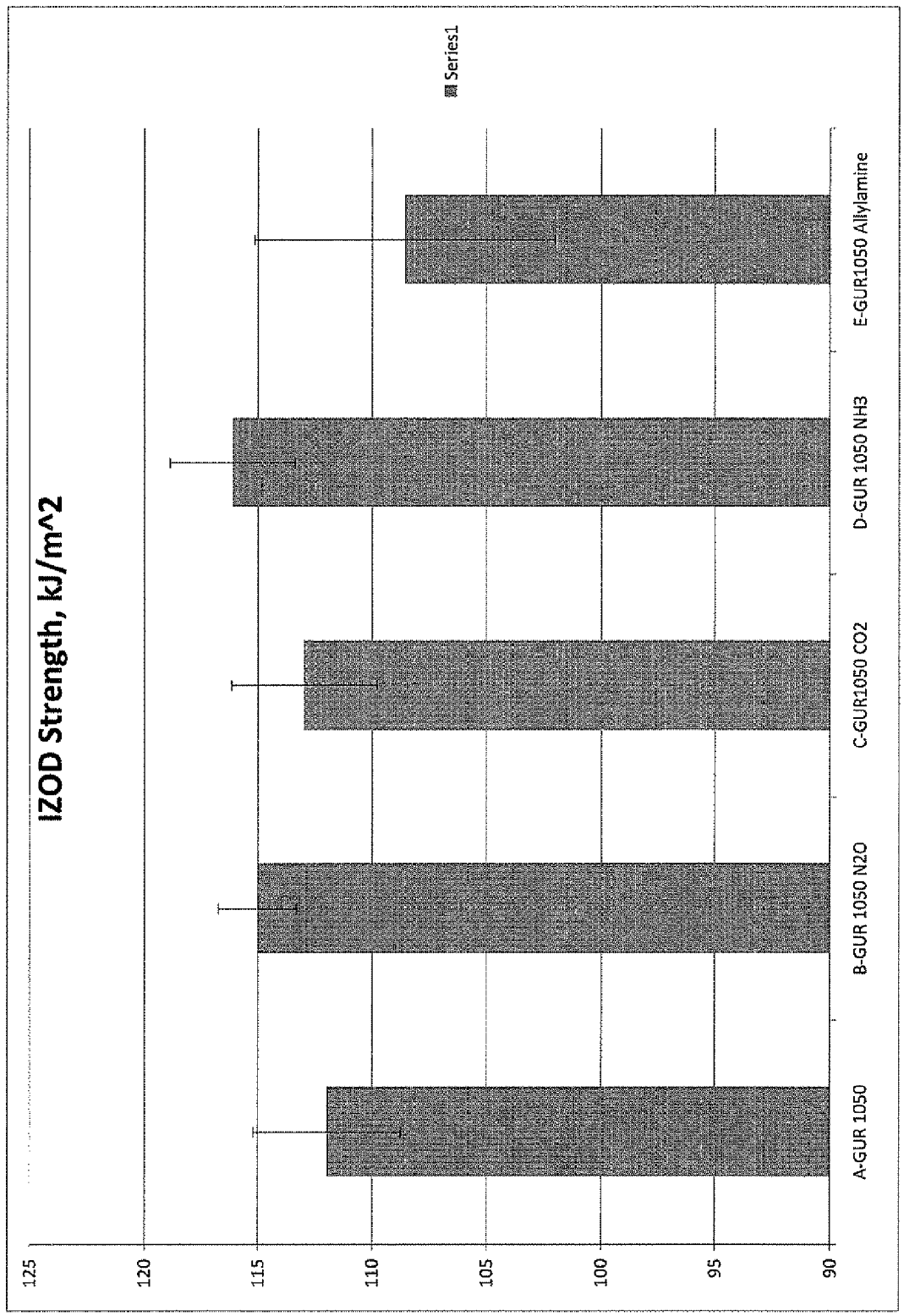
FIGS. 8 and 9 are graphs showing the IZOD strength of samples made from unmodified UHMWPE powder and samples made from plasma modified UHMWPE powder.
Figure 9:
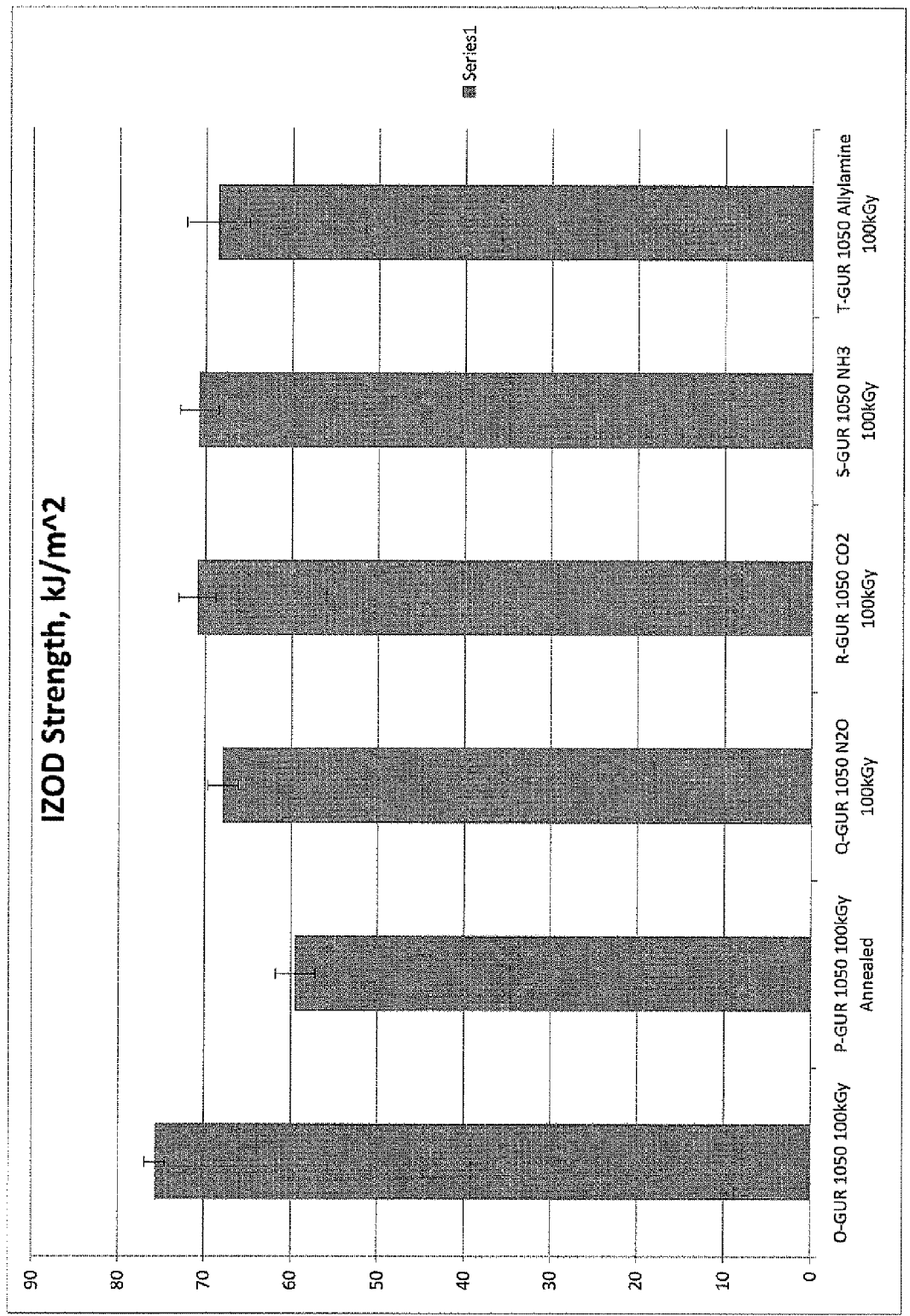

FIGS. 8 and 9 are bar graphs illustrating the results of the IZOD strength tests.

Contact Angle Test Results

Contact angle measurements, which measure the angle between the surface of a liquid solvent (e.g. water, serum) and the surface of the polymer substrate at the line of contact, were conducted on samples A-E and Q-T in order to test the lubricity of the surface layer of flats machined from the middle of the puck. In general, the lower the contact angle, the more wettable the surface, which indicates greater lubricity with the solvent. In the present case, deionized water, phosphate buffered saline and bovine synovial fluid were used as solvents. The bovine synovial fluid used is available from Animal Technologies, Inc., located in Tyler, Tex. Addition- Wear Testing Samples AA-JJ were subjected to wear testing, in terms of weight loss, on a custom built pin-on-flat (POF) twelve-station screening device located in the Tribology Testing Laboratory at Zimmer, Inc. (Warsaw, Ind., USA). Briefly, the above described compression molded pucks of Samples CC-LL were machined to produce a test pin having a diameter of 9.07 mm and a length of 9.55 mm.

Figure 11:
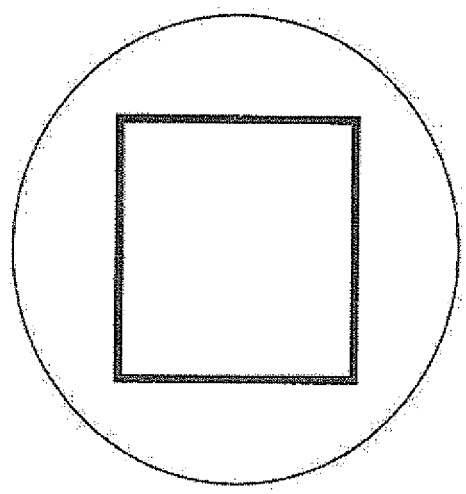
FIG. 11 is a schematic drawing of the square waveform utilized in wear testing.
Figure 12:
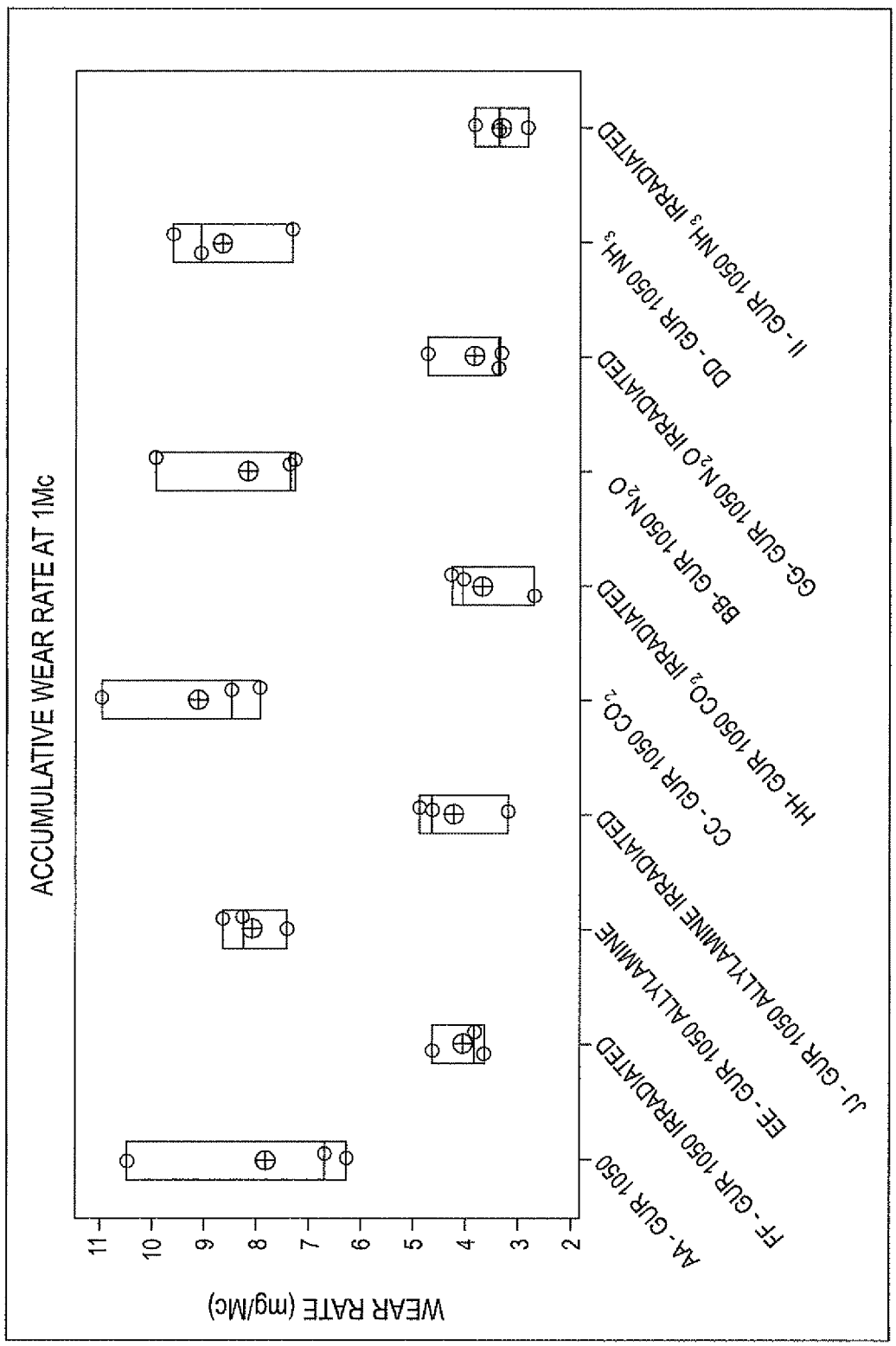
FIG. 12 is a graph showing the accumulative wear rate at one million cycles of samples made from unmodified UHMWPE powder and samples made from plasma modified UHMWPE powder.

During testing, the pins were articulated against a CoCr disk having an $R_a$ of <0.02 µm to test wear properties in terms of weight. The test was conducted at constant force of 445 N, at 1.0 Hz for 75,000 cycles, and in undiluted bovine calf serum including EDTA (disodium salt, 7.9 g/l) and Sodium Azide (3.0 g/l). The CoCr disks were articulated against the pin surface in the 15 mm×15mm square waveform as shown in FIG. 11. The pins were removed from the device and cleaned, dried and weighed every 25,000 cycles. Additionally, the bovine serum was changed every 25,000 cycles. Three runs of each sample were used in this wear testing and Table 6 shows the average weight loss of the three specimens for each sample. FIG. 12 illustrates the accumulative wear rate at one million cycles.

TABLE 6

| SAMPLE | MATERIAL | AVERAGE PIN WEIGHT LOSS AT 25K CYCLES | AVERAGE PIN WEIGHT LOSS AT 50K CYCLES | AVERAGE PIN WEIGHT LOSS AT 75K CYCLES |
|---|---|---|---|---|
| AA | GUR 1050 | 1.99 mg | 4.00 mg | 6.25 mg |
| BB | GUR 1050 $N_2O$ | 1.50 mg | 3.25 mg | 5.11 mg |
| CC | GUR 1050 $CO_2$ | 1.81 mg | 3.72 mg | 5.66 mg |
| DD | GUR 1050 $NH_3$ | 0.65 mg | 1.49 mg | 2.38 mg |
| EE | GUR 1050 Amine | 1.51 mg | 3.36 mg | 5.94 mg |
| FF | GUR 1050 Irradiated | 0.56 mg | 1.37 mg | 2.56 mg |
| II | GUR 1050 $NH_3$ Irradiated | 1.54 mg | 3.47 mg | 5.76 mg |
| JJ | GUR 1050 Amine Irradiated | 0.98 mg | 2.39 mg | 3.71 mg |

Plasma Spraying

The polymeric articles disclosed herein may also be constructed by plasma spraying, thermal deposition corona spraying or combinations thereof. In one embodiment, a plasma spraying process is employed to modify polymer powder to include selected functional groups.

Plasma spraying or thermal deposition are known coating processes that are used to apply a coating or layer to a substrate or work piece. In general, plasma spraying includes spraying of molten or softened material onto a surface to provide a layer or coating on the surface. In the context of polymer coatings, polymer powders are injected into a very high temperature plasma flame, where the polymer is heated and sprayed at high velocity onto a substrate. The substrate may be, but is not limited to, tribological components such as metal and/or ceramic substrates. In other embodiments, metal backing (e.g. plates or shields) may be used as the substrate. In further embodiments, the substrate may include a trabecular metal or fiber metal.

Figure 13:
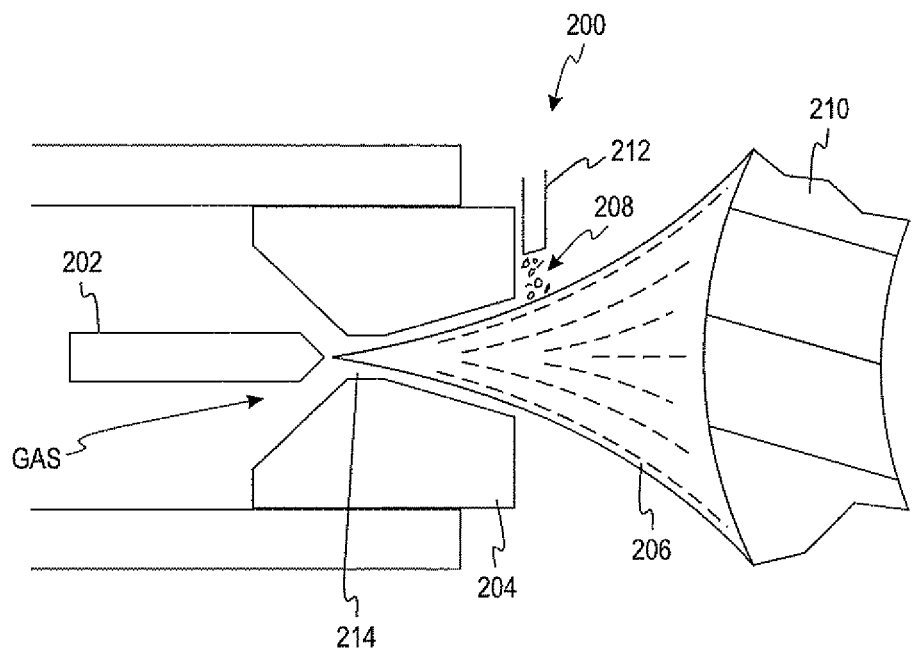
FIG. 13 is a schematic drawing of a plasma spray device.

FIG. 13 is a schematic illustration of a plasma spray 200 suitable for treating and modifying the substrates of orthopedic implants. Plasma spray 200 includes an inner cathode 202 surrounded by an outer anode 204 which is shaped to form a constricting nozzle 214. The anode 204 is typically made of cooper and the cathode 202 is typically made of tungsten. Gas is flowed between the cathode 202 and anode 204 as a direct current is maintained between the cathode 202 and anode 204. A high voltage discharge causes localized ionization and a path for an arc to form between the cathode 202 and anode 204. The arc causes the gas to form a plasma. The plasma exits the anode as a flame 206. In the embodiment shown, the polymer powder 208 is feed into the flame by a feeding tube 212. However, the polymer powder 208 may be feed into the sprayer at any suitable location and by any suitable method. The powder 208 injected is rapidly heated and accelerated to a high velocity. The heated, high velocity powder impacts the substrate 210, where it cools to create a coating or layer.

The gases used in the plasma spray modification methods disclosed herein may be a mixture of inert gases with reactive gases, may be a mixture of different reactive gases or may be only a single reactive gas. Reactive gases are those that will produce a reactive species when formed into plasma or when exposed to a plasma. Such reactive gases include but are not limited to ammonia, sulfur trioxide, carbon tetrafluoride and ethylene oxide. The functional groups produced may include one or more amines, amides, hydroxyl, carbonyl, aldehyde, carboxylate, carboxyl, ether, ester, sulfonic, epoxide, phosphate, perfluoro, etc. When the reactive gases are mixed with or exposed to a plasma created by an inert gas, such inert gases may include argon, helium, hydrogen and nitrogen.

The polymer powder may be any polymer powder suitable for use in a plasma spray process. For example, the polymer powder may be UHMWPE or polyaryletherketones (such as PEEK or PEKK). When the polymer powder is feed into the plasma, the polymer and the reactive species will react together in the plasma to modify the polymer prior to the polymer being deposited onto a substrate. In other words, the polymer will be modified to include functional groups prior to deposition on the substrate, thereby resulting in a polymer layer or coating that includes modification throughout the layer.

Further, the type and amount of reactive gases employed in the spraying process can be varied during the process to produce polymeric articles having different functional groups or varying amounts of functional groups throughout the body. In one embodiment, the gases may be switched during the spraying process to create a multilayered bulk construct. For example, one type of reactive gas, such as $PCl_3$, may be used to construct the bottom of a polymeric article to may it osteoconductive and another reactive gas, such as, $SO_2$ may be employed to make the top of the polymeric article cartilage friendly.

Compression Molding of Polymer Materials

Some polymers that have been functionalized or modified may be difficult to melt process. Thus, materials and articles made of such polymers are only surfaced modified or functionalized after the desired shape is produced. As discussed above, as the surface is worn away, so are the functional groups, thus reducing the effectiveness of the surface modification over time.

Another embodiment of forming the polymer articles disclosed herein includes a process of modification wherein a porous polymeric article is subjected to functionalization treatments. Such treatments may include sulfonation, plasma treatments, ketone-to-ether reactions, etc. Sulfonation is a known process and described in *Sulfonation of Poly (Ether Ether Ketone) (PEEK): Kinetic Study and Characterization*, Huang et al., Journal of Applied Polymer Science, Vol. 82 Issue 11, December 2001, pp. 2651-2660 and *Synthesis and Characterization of Homogeneously Sulfonated Poly (Ether Ether Ketone) Membranes: Effect of Casting Solvent*, Do et al., Journal of Applied Polymer Science, Vol. 110, Issue 3, November 2009, pp. 1763-1770, which are incorporated by reference herein.

The pores of the porous polymeric article allow the treatments to penetrate into the polymeric article and bond and introduce functional groups to the interior portions of the porous polymeric article. After the porous body has been subjected to modification treatments, it is compression molded to collapse the pores resulting in a polymeric article that has functional or reactive groups distributed substantially throughout the article. The modified porous body may be compression molded into a final implant shape or configuration or it may compression molded into a shape that requires further processing.

In one embodiment, a PEEK or PEKK polymeric article having functional groups throughout is formed. A porous PEEK or PEKK polymeric article, which may be obtained for example from Porogen located in Woburn, Mass., USA, is subjected to a modification treatment to bond or otherwise attach functional groups to a polymeric article. As discussed above, the pores of the porous PEEK or PEKK polymeric article allow modification treatment of interior regions to bond functional groups to the inner portions or layers of the porous PEEK or PEKK body. The modification treatment may include but is not limited to sulfonation, plasma treatment or ketone-to-ether treatments. After the modification treatment, the porous body is compression molded to collapse the pores and form a PEEK or PEKK polymeric article having functional groups bonded to inner portions of the polymeric article.

Ultrasonic Compression Molding of Polymer Materials

Another way by which a polymeric material or article may be modified is by molding a polymer which employ applying ultrasonic energy to the polymer during the molding process. These ultrasonic molding methods may be used, for example, to consolidate (compression mold or ram extrusion) UHMWPE.

Consolidation UHMWPE involves self-diffusion of polymer chains in which the polymer chains of adjacent particles intermingle and entangle on the molecular level. In order for intermingling to occur, the particles must be in close proximity and the polymer chains must have some mobility. Accordingly, intermingling of adjacent particles is promoted by applying elevated temperatures and pressure. The elevated pressure places the grain boundaries or interfacing surfaces of adjacent particles in close proximity, and elevating the temperature increases the mobility of the polymer chains. Because consolidation involves diffusion, the process requires maintaining the elevated temperature and pressures for a sufficient time to allow the polymer chains to migrate across the grain boundaries. Although the polymer chains migrate and intermingle, the grain boundaries are retained for the most part. The grain boundaries of a consolidated polymeric UHMWPE body represent the weakest point in the material.

In the methods disclosed herein, ultrasonic energy, such as sound waves, may be applied to the UHMWPE during the consolidation process to enhance or improve the intermingling of the polymer chains of adjacent particles. In one embodiment, the ultrasonic energy may be in the form of high energy or high frequency sound waves. The application of ultrasonic energy can create localized heating and provide energy that promotes polymer chain mobility and entanglement.

Figure 14:
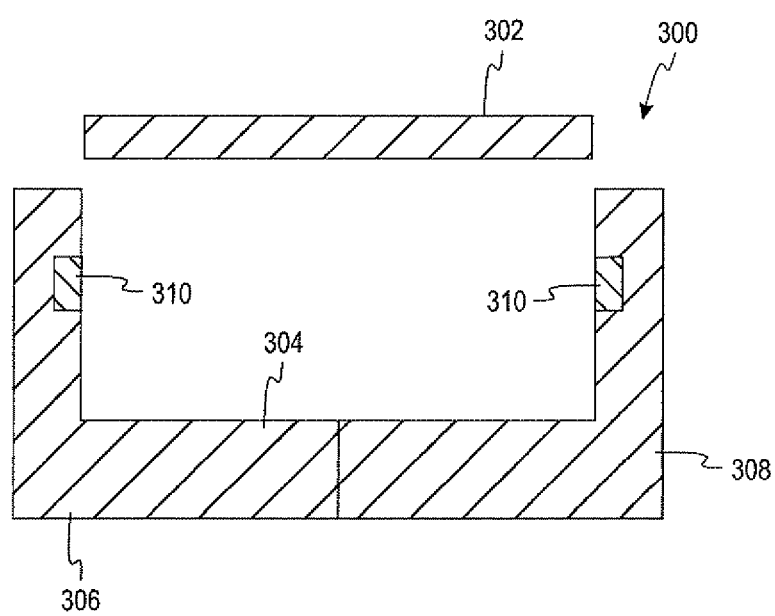
FIG. 14 is a schematic illustration of a mold cavity fitted with ultrasonic energy devices.

The ultrasonic energy can be applied to the UHMWPE during consolidation by any suitable method. For example, ultrasonic horns may be fitted into a compression mold cavity. FIG. 14 illustrates one example of an embodiment of a mold 300 that could be used in an ultrasonic molding process. The mold 300 includes a top portion 302 and bottom portion 304, which open and close to form the mold. In this embodiment, the bottom portion 304 includes two sections 306 and 308 which may separate to release the molded material. The mold 300 also includes ultrasonic energy generators 310 located in the bottom portion 304 of the mold. However, the ultrasonic energy generators 310 may be places in any suitable position. In one embodiment, the ultrasonic energy generators 310 may be specifically aimed direct ultrasonic energy to a particular portion of the molded material.

In a compression molding process, UHMWPE is placed into the mold and placed under elevated temperature and pressure, as done in conventional compressing molding methods. When the polymer is in the melt stage, ultrasonic energy is applied, for example through activation of ultrasonic horns, to provide energy that promotes greater diffusion of polymer chains of adjacent polymer particles. Any suitable amount of ultrasonic energy may be applied during the process. In one embodiment, the ultrasonic energy may be between about 10 kHz and about 100 kHz, and more preferably about 20-40 kHz. The ultrasonic energy may also promote diffusion of polymer chains from two distance boundary layers.

Using ultrasonic energy can provide several benefits, including but not limited to, reduced cycle times, enhanced chain entanglement and increased material strength. Further, because the application of ultrasonic energy reduces air bubbles and voids, the application of ultrasonic energy could be used to reduce the amount of oxygen within the molded material, which would assist in reducing oxidation of the material. This is believed to be particularly useful when molding UHMWPE which has been blended with an antioxidant, such as Vitamin E which is susceptible to oxidation. Also, the ultrasonic energy could be employed to induce crosslinking. The ultrasonic energy could be such that it results in chain scission and cross-linking of the UHMWPE.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A method of forming a polymeric article suitable for use as an orthopedic implant, the method comprising:
   providing or receiving particles of a polymer resin;
   exposing the particles of the polymer resin to a plasma, the plasma reacting with the particles of the polymer resin to bond one or more selected reactive groups to the particles; and
   molding a polymeric article from the polymer resin after exposing the polymer resin to the plasma.

2. The method of claim 1, wherein the plasma is formed from a gas selected from the group consisting of nitric oxide, carbon dioxide, ammonia, allylamine, and combinations thereof.

3. The method of claim 1, wherein the one or more selected reactive groups are selected from the group consisting of amines, amides, imides, carboxyl, carbonyl, hydroxyl, sulfonates, phosphates, perfluoro and combinations thereof.

4. The method of claim 1, further comprising blending the particles of the polymer resin with an additive.

5. The method of claim 4, wherein the additive is selected from the group consisting of an antioxidant, an antibiotic, an antimicrobial, and an anti-inflammatory.

6. The method of claim 4, wherein the blending occurs after exposure of the particles to the plasma.

7. The method of claim 1, wherein molding comprises compression molding the polymer resin.

8. The method of claim 1, wherein the polymer resin is selected from the group consisting of as polyethylene, ultrahigh molecular weight polyethylene, polyaryletherketones, polypropylene, polyurethanes, acrylic resin, polyethylene-co-vinyl alcohol, nylon, polysulfones, polycarbonates, and polyacrylamides or combinations thereof.

9. The method of claim 1, wherein the particles of the polymer resin include polymer molecules, and the method further comprises crosslinking the polymer molecules prior to or after molding.

10. The method of claim 9, wherein the crosslinking comprises irradiating the polymeric article.

11. The method of claim 9, wherein the reactive groups are crosslinking agents and crosslink the polymer.

12. A method of forming a polymeric article suitable for use as an orthopedic implant, the method comprising:
providing or receiving particles of a first polymer resin;
exposing particles of a first polymer resin to a first plasma, including reacting the particles of the first polymer resin with the first plasma to bond one or more selected reactive groups to the particles of the first polymer resin;
exposing particles of a second polymer resin to a second plasma, including reacting the particles of the second polymer resin to bond one or more selected reactive groups to the particles of the second resin; and
consolidating the first and second polymer resins to form a polymeric article that includes different reactive groups located in different regions of the polymer article.

13. The method of claim 12, wherein consolidating the first and second polymer resins comprises mixing the first and second resins together prior to forming the polymeric article.

14. The method of claim 12, wherein the first polymer resin and the second polymer resin comprise the same polymer.

15. A method of forming a polymeric article suitable for use as a medical implant, the method comprising:
providing a plasma-modified polymer resin having one or more reactive groups bonded to particles of the plasma-modified polymer resin; and
molding a polymeric article from the plasma-modified polymer resin, the one or more reactive groups located at least at an interior region of the polymeric article.

16. The method of claim 15, wherein the polymer resin is selected from the group consisting of polyethylene, ultrahigh molecular weight polyethylene, polyaryletherketones, polypropylene, and combinations thereof.

17. An orthopedic implant, comprising:
an article comprising a polymer, the article having an outer surface and an interior region;
the polymer including a plurality of polymer molecules having one or more reactive groups bonded thereto, the one or more reactive groups providing one or more properties selected from the group consisting of crosslinking, lubricity, wettability, hydrophobicity, hydrophilicity, wear resistance, tissue attachment, protein binding, reducing adverse biological reactions, reducing a chronic inflammatory response, reducing production of degrading enzymes and destructive species, and combinations thereof; and
the plurality of polymer molecules being located at least at the interior region of the polymeric article.

18. The implant of claim 17, wherein the one or more reactive groups are located substantially throughout the interior region and at the outer surface of the article.

19. The implant of claim 17, wherein the one or more reactive groups are located in selective portions of the polymeric article.

20. The method of claim 15, wherein the one or more reactive groups provide one or more properties to the polymeric article, the one or more properties selected from the group consisting of crosslinking, lubricity, wettability, hydrophobicity, hydrophilicity, wear resistance, tissue attachment, protein binding, reducing adverse biological reactions, reducing a chronic inflammatory response, reducing production of degrading enzymes and destructive species, and combinations thereof.

* * * * *